(12) United States Patent
Ou et al.

(10) Patent No.: US 10,076,285 B2
(45) Date of Patent: Sep. 18, 2018

(54) SENSOR FAULT DETECTION USING ANALYTE SENSOR DATA PATTERN COMPARISON

(71) Applicant: Abbott Diabetes Care Inc., Alameda, CA (US)

(72) Inventors: Junli Ou, Pleasanton, CA (US); Erwin Satrya Budiman, Fremont, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 419 days.

(21) Appl. No.: 14/771,804

(22) PCT Filed: Mar. 13, 2014

(86) PCT No.: PCT/US2014/026845
§ 371 (c)(1),
(2) Date: Sep. 1, 2015

(87) PCT Pub. No.: WO2014/152034
PCT Pub. Date: Sep. 25, 2014

(65) Prior Publication Data
US 2016/0022221 A1    Jan. 28, 2016

Related U.S. Application Data

(60) Provisional application No. 61/794,793, filed on Mar. 15, 2013.

(51) Int. Cl.
*A61B 5/00* (2006.01)
*A61B 5/145* (2006.01)
*A61B 5/1459* (2006.01)

(52) U.S. Cl.
CPC ........ *A61B 5/7271* (2013.01); *A61B 5/14532* (2013.01); *A61B 5/742* (2013.01); *A61B 5/1459* (2013.01); *A61B 2560/0228* (2013.01)

(58) Field of Classification Search
CPC ....... A61B 5/00; A61B 5/145; A61B 5/14532; A61B 5/7271; A61B 5/742; A61B 5/1459; A61B 2560/0228
See application file for complete search history.

(56) References Cited

U.S. PATENT DOCUMENTS 3,581,062 A    5/1971  Aston
3,926,760 A    12/1975 Allen et al.
(Continued)

FOREIGN PATENT DOCUMENTS

EP    0098592    1/1984
EP    0127958    12/1984
(Continued)

OTHER PUBLICATIONS

PCT Application No. PCT/US2014/026845, International Preliminary Report on Patentability and Written Opinion of the International Searching Authority dated Sep. 24, 2015.
(Continued)

*Primary Examiner* — Navin Natnithithadha
*Assistant Examiner* — Eric Messersmith
(74) *Attorney, Agent, or Firm* — Arent Fox LLP

(57) ABSTRACT

Analyte sensor faults are detected. Datasets of glucose values sensor electronics are coupled to a glucose sensor in fluid contact with interstitial fluid under a skin surface. Baseline median glucose value and glucose variability values are computed, based on the first dataset. A baseline data point is stored. Evaluation median glucose value and variability are computed, based on the second dataset of glucose values. An evaluation data point is stored. A magnitude of a vector that extends between the baseline data point and the evaluation data point is computed. A component of the magnitude of the vector that is parallel to a hypoglycemia risk contour line is computed and compared to a predefined
(Continued)

threshold value. An indication that a sensor fault has been detected if the component is greater than a threshold is displayed.

23 Claims, 11 Drawing Sheets

(56) References Cited

U.S. PATENT DOCUMENTS

| | | | |
|---|---|---|---|
| 3,949,388 A | 4/1976 | Fuller | |
| 3,960,497 A | 6/1976 | Acord et al. | |
| 3,978,856 A | 9/1976 | Michel | |
| 4,036,749 A | 7/1977 | Anderson | |
| 4,055,175 A | 10/1977 | Clemens et al. | |
| 4,129,128 A | 12/1978 | McFarlane | |
| 4,245,634 A | 1/1981 | Albisser et al. | |
| 4,327,725 A | 5/1982 | Cortese et al. | |
| 4,344,438 A | 8/1982 | Schultz | |
| 4,349,728 A | 9/1982 | Phillips et al. | |
| 4,373,527 A | 2/1983 | Fischell | |
| 4,392,849 A | 7/1983 | Petre et al. | |
| 4,425,920 A | 1/1984 | Bourland et al. | |
| 4,441,968 A | 4/1984 | Emmer et al. | |
| 4,462,048 A | 7/1984 | Ross | |
| 4,478,976 A | 10/1984 | Goertz et al. | |
| 4,494,950 A | 1/1985 | Fischell | |
| 4,509,531 A | 4/1985 | Ward | |
| 4,527,240 A | 7/1985 | Kvitash | |
| 4,538,616 A | 9/1985 | Rogoff | |
| 4,545,382 A | 10/1985 | Higgins et al. | |
| 4,619,793 A | 10/1986 | Lee | |
| 4,671,288 A | 6/1987 | Gough | |
| 4,703,756 A | 11/1987 | Gough et al. | |
| 4,711,245 A | 12/1987 | Higgins et al. | |
| 4,731,051 A | 3/1988 | Fischell | |
| 4,731,726 A | 3/1988 | Allen, III | |
| 4,749,985 A | 6/1988 | Corsberg | |
| 4,757,022 A | 7/1988 | Shults et al. | |
| 4,759,366 A | 7/1988 | Callaghan | |
| 4,772,445 A * | 9/1988 | Nasrallah | G01D 3/02 318/563 |
| 4,777,953 A | 10/1988 | Ash et al. | |
| 4,779,618 A | 10/1988 | Mund et al. | |
| 4,854,322 A | 8/1989 | Ash et al. | |
| 4,871,351 A | 10/1989 | Feingold | |
| 4,890,620 A | 1/1990 | Gough | |
| 4,925,268 A | 5/1990 | Iyer et al. | |
| 4,947,845 A | 8/1990 | Davis | |
| 4,953,552 A | 9/1990 | DeMarzo | |
| 4,986,271 A | 1/1991 | Wilkins | |
| 4,995,402 A | 2/1991 | Smith et al. | |
| 5,000,180 A | 3/1991 | Kuypers et al. | |
| 5,002,054 A | 3/1991 | Ash et al. | |
| 5,019,974 A | 5/1991 | Beckers | |
| 5,050,612 A | 9/1991 | Matsumura | |
| 5,055,171 A | 10/1991 | Peck | |
| 5,068,536 A | 11/1991 | Rosenthal | |
| 5,077,476 A | 12/1991 | Rosenthal | |
| 5,082,550 A | 1/1992 | Rishpon et al. | |
| 5,106,365 A | 4/1992 | Hernandez | |
| 5,113,869 A | 5/1992 | Nappholz et al. | |
| 5,122,925 A | 6/1992 | Inpyn | |
| 5,135,004 A | 8/1992 | Adams et al. | |
| 5,148,812 A | 9/1992 | Verrier et al. | |
| 5,165,407 A | 11/1992 | Wilson et al. | |
| 5,199,428 A | 4/1993 | Obel et al. | |
| 5,202,261 A | 4/1993 | Musho et al. | |
| 5,203,326 A | 4/1993 | Collins | |
| 5,204,264 A | 4/1993 | Kaminer et al. | |
| 5,210,778 A | 5/1993 | Massart | |
| 5,231,988 A | 8/1993 | Wernicke et al. | |
| 5,246,867 A | 9/1993 | Lakowicz et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,279,294 A | 1/1994 | Anderson et al. | |
| 5,285,792 A | 2/1994 | Sjoquist et al. | |
| 5,293,877 A | 3/1994 | O'Hara et al. | |
| 5,299,571 A | 4/1994 | Mastrototaro | |
| 5,313,953 A | 5/1994 | Yomtov et al. | |
| 5,320,715 A | 6/1994 | Berg | |
| 5,320,725 A | 6/1994 | Gregg et al. | |
| 5,322,063 A | 6/1994 | Allen et al. | |
| 5,328,460 A | 7/1994 | Lord et al. | |
| 5,330,634 A | 7/1994 | Wong et al. | |
| 5,340,722 A | 8/1994 | Wolfbeis et al. | |
| 5,342,789 A | 8/1994 | Chick et al. | |
| 5,356,786 A | 10/1994 | Heller et al. | |
| 5,360,404 A | 11/1994 | Novacek et al. | |
| 5,365,426 A | 11/1994 | Siegel et al. | |
| 5,372,427 A | 12/1994 | Padovani et al. | |
| 5,376,070 A | 12/1994 | Purvis et al. | |
| 5,379,238 A | 1/1995 | Stark | |
| 5,384,547 A | 1/1995 | Lynk et al. | |
| 5,390,671 A | 2/1995 | Lord et al. | |
| 5,391,250 A | 2/1995 | Cheney, II et al. | |
| 5,400,795 A | 3/1995 | Murphy et al. | |
| 5,408,999 A | 4/1995 | Singh et al. | |
| 5,411,647 A | 5/1995 | Johnson et al. | |
| 5,425,749 A | 6/1995 | Adams | |
| 5,425,868 A | 6/1995 | Pedersen | |
| 5,431,160 A | 7/1995 | Wilkins | |
| 5,431,921 A | 7/1995 | Thombre | |
| 5,438,983 A | 8/1995 | Falcone | |
| 5,462,645 A | 10/1995 | Albery et al. | |
| 5,472,317 A | 12/1995 | Field et al. | |
| 5,489,414 A | 2/1996 | Schreiber et al. | |
| 5,497,772 A | 3/1996 | Schulman et al. | |
| 5,505,828 A | 4/1996 | Wong et al. | |
| 5,507,288 A | 4/1996 | Bocker et al. | |
| 5,509,410 A | 4/1996 | Hill et al. | |
| 5,514,718 A | 5/1996 | Lewis et al. | |
| 5,520,191 A | 5/1996 | Karlsson et al. | |
| 5,531,878 A | 7/1996 | Vadgama et al. | |
| 5,532,686 A | 7/1996 | Urbas et al. | |
| 5,543,326 A | 8/1996 | Heller et al. | |
| 5,552,997 A | 9/1996 | Massart | |
| 5,568,400 A | 10/1996 | Stark et al. | |
| 5,568,806 A | 10/1996 | Cheney, II et al. | |
| 5,569,186 A | 10/1996 | Lord et al. | |
| 5,582,184 A | 12/1996 | Erickson et al. | |
| 5,586,553 A | 12/1996 | Halili et al. | |
| 5,593,852 A | 1/1997 | Heller et al. | |
| 5,601,435 A | 2/1997 | Quy | |
| 5,609,575 A | 3/1997 | Larson et al. | |
| 5,628,310 A | 5/1997 | Rao et al. | |
| 5,628,890 A | 5/1997 | Carter et al. | |
| 5,634,468 A | 6/1997 | Platt et al. | |
| 5,640,954 A | 6/1997 | Pfeiffer et al. | |
| 5,653,239 A | 8/1997 | Pompei et al. | |
| 5,660,163 A | 8/1997 | Schulman et al. | |
| 5,665,222 A | 9/1997 | Heller et al. | |
| 5,707,502 A | 1/1998 | McCaffrey et al. | |
| 5,711,001 A | 1/1998 | Bussan et al. | |
| 5,711,861 A | 1/1998 | Ward et al. | |
| 5,720,295 A | 2/1998 | Greenhut et al. | |
| 5,724,030 A | 3/1998 | Urbas et al. | |
| 5,733,259 A | 3/1998 | Valcke et al. | |
| 5,735,285 A | 4/1998 | Albert et al. | |
| 5,741,211 A | 4/1998 | Renirie et al. | |
| 5,749,907 A | 5/1998 | Mann | |
| 5,772,586 A | 6/1998 | Heinonen et al. | |
| 5,785,660 A | 7/1998 | van Lake et al. | |
| 5,791,344 A | 8/1998 | Schulman et al. | |
| 5,792,065 A | 8/1998 | Xue et al. | |
| 5,804,047 A | 9/1998 | Karube et al. | |
| 5,820,551 A | 10/1998 | Hill et al. | |
| 5,822,715 A | 10/1998 | Worthington et al. | |
| 5,891,047 A | 4/1999 | Lander et al. | |
| 5,891,049 A | 4/1999 | Cyrus et al. | |
| 5,899,855 A | 5/1999 | Brown | |
| 5,914,026 A | 6/1999 | Blubaugh, Jr. et al. | |

(56) References Cited

U.S. PATENT DOCUMENTS

| | | |
|---|---|---|
| 5,918,603 A | 7/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,951,485 A | 9/1999 | Cyrus et al. |
| 5,957,854 A | 9/1999 | Besson et al. |
| 5,960,797 A | 10/1999 | Kramer et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,016,443 A | 1/2000 | Ekwall et al. |
| 6,021,350 A | 2/2000 | Mathson |
| 6,024,699 A | 2/2000 | Surwit et al. |
| 6,038,469 A | 3/2000 | Karlsson et al. |
| 6,049,727 A | 4/2000 | Crothall |
| 6,071,391 A | 6/2000 | Gotoh et al. |
| 6,073,031 A | 6/2000 | Helstab et al. |
| 6,083,710 A | 7/2000 | Heller et al. |
| 6,088,608 A | 7/2000 | Schulman et al. |
| 6,091,976 A | 7/2000 | Pfeiffer et al. |
| 6,091,987 A | 7/2000 | Thompson |
| 6,093,172 A | 7/2000 | Funderburk et al. |
| 6,103,033 A | 8/2000 | Say et al. |
| 6,108,577 A | 8/2000 | Benser |
| 6,112,116 A | 8/2000 | Fischell |
| 6,115,622 A | 9/2000 | Minoz |
| 6,115,628 A | 9/2000 | Stadler et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,128,526 A | 10/2000 | Stadler et al. |
| 6,130,623 A | 10/2000 | MacLellan et al. |
| 6,134,461 A | 10/2000 | Say et al. |
| 6,143,164 A | 11/2000 | Heller et al. |
| 6,144,837 A | 11/2000 | Quy |
| 6,144,871 A | 11/2000 | Saito et al. |
| 6,159,147 A | 12/2000 | Lichter et al. |
| 6,161,095 A | 12/2000 | Brown |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,223,283 B1 | 4/2001 | Chaiken et al. |
| 6,233,471 B1 | 5/2001 | Berner et al. |
| 6,233,486 B1 | 5/2001 | Ekwall et al. |
| 6,248,067 B1 | 6/2001 | Causey, III et al. |
| 6,249,705 B1 | 6/2001 | Snell |
| 6,254,586 B1 | 7/2001 | Mann et al. |
| 6,256,538 B1 | 7/2001 | Ekwall |
| 6,264,606 B1 | 7/2001 | Ekwall et al. |
| 6,270,455 B1 | 8/2001 | Brown |
| 6,272,379 B1 | 8/2001 | Fischell et al. |
| 6,275,717 B1 | 8/2001 | Gross et al. |
| 6,283,761 B1 | 9/2001 | Joao |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,299,757 B1 | 10/2001 | Feldman et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,338,790 B1 | 1/2002 | Feldman et al. |
| 6,348,640 B1 | 2/2002 | Navot et al. |
| 6,359,444 B1 | 3/2002 | Grimes |
| 6,360,888 B1 | 3/2002 | McIvor et al. |
| 6,361,503 B1 | 3/2002 | Starobin et al. |
| 6,366,794 B1 | 4/2002 | Moussy et al. |
| 6,377,828 B1 | 4/2002 | Chaiken et al. |
| 6,377,852 B1 | 4/2002 | Bornzin et al. |
| 6,377,894 B1 | 4/2002 | Deweese et al. |
| 6,379,301 B1 | 4/2002 | Worthington et al. |
| 6,381,493 B1 | 4/2002 | Stadler et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,413,393 B1 | 7/2002 | Van Antwerp et al. |
| 6,416,471 B1 | 7/2002 | Kumar et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,461,496 B1 | 10/2002 | Feldman et al. |
| 6,471,689 B1 | 10/2002 | Joseph et al. |
| 6,478,736 B1 | 11/2002 | Mault |
| 6,484,046 B1 | 11/2002 | Say et al. |
| 6,496,729 B2 | 12/2002 | Thompson |
| 6,497,655 B1 | 12/2002 | Linberg et al. |
| 6,501,983 B1 | 12/2002 | Natarajan et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,520,326 B2 | 2/2003 | McIvor et al. |
| 6,540,891 B1 | 4/2003 | Stewart et al. |
| 6,544,212 B2 | 4/2003 | Galley et al. |
| 6,549,796 B2 | 4/2003 | Sohrab |
| 6,551,494 B1 | 4/2003 | Heller et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,574,490 B2 | 6/2003 | Abbink et al. |
| 6,574,510 B2 | 6/2003 | Von Arx et al. |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,616,819 B1 | 9/2003 | Liamos et al. |
| 6,618,934 B1 | 9/2003 | Feldman et al. |
| 6,622,045 B2 | 9/2003 | Snell et al. |
| 6,633,772 B2 | 10/2003 | Ford et al. |
| 6,635,014 B2 | 10/2003 | Starkweather et al. |
| 6,635,167 B1 | 10/2003 | Batman et al. |
| 6,641,533 B2 | 11/2003 | Causey, III et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulson et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,721,582 B2 | 4/2004 | Trepagnier et al. |

(56) References Cited

U.S. PATENT DOCUMENTS

| | | |
|---|---|---|
| 6,730,200 B1 | 5/2004 | Stewart et al. |
| 6,731,976 B2 | 5/2004 | Penn et al. |
| 6,731,985 B2 | 5/2004 | Poore et al. |
| 6,733,446 B2 | 5/2004 | Lebel et al. |
| 6,735,183 B2 | 5/2004 | O'Toole et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,749,740 B2 | 6/2004 | Liamos et al. |
| 6,758,810 B2 | 7/2004 | Lebel et al. |
| 6,764,581 B1 | 7/2004 | Forrow et al. |
| 6,770,030 B1 | 8/2004 | Schaupp et al. |
| 6,773,671 B1 | 8/2004 | Lewis et al. |
| 6,790,178 B1 | 9/2004 | Mault et al. |
| 6,804,558 B2 | 10/2004 | Haller et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,912,413 B2 | 6/2005 | Rantala et al. |
| 6,923,763 B1 | 8/2005 | Kovatchev et al. |
| 6,923,764 B2 | 8/2005 | Aceti et al. |
| 6,931,327 B2 | 8/2005 | Goode, Jr. et al. |
| 6,932,892 B2 | 8/2005 | Chen et al. |
| 6,932,894 B2 | 8/2005 | Mao et al. |
| 6,936,006 B2 | 8/2005 | Sabra |
| 6,940,403 B2 | 9/2005 | Kail, IV |
| 6,941,163 B2 | 9/2005 | Ford et al. |
| 6,942,518 B2 | 9/2005 | Liamos et al. |
| 6,950,708 B2 | 9/2005 | Bowman, IV et al. |
| 6,954,662 B2 | 10/2005 | Freger et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,009,511 B2 | 3/2006 | Mazar et al. |
| 7,010,345 B2 | 3/2006 | Hill et al. |
| 7,011,630 B2 | 3/2006 | Desai et al. |
| 7,016,713 B2 | 3/2006 | Gardner et al. |
| 7,016,720 B2 | 3/2006 | Kroll |
| 7,020,508 B2 | 3/2006 | Stivoric et al. |
| 7,022,072 B2 | 4/2006 | Fox et al. |
| 7,022,219 B2 | 4/2006 | Mansouri et al. |
| 7,024,236 B2 | 4/2006 | Ford et al. |
| 7,024,245 B2 | 4/2006 | Lebel et al. |
| 7,025,425 B2 | 4/2006 | Kovatchev et al. |
| 7,029,443 B2 | 4/2006 | Kroll |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,287 B1 | 5/2006 | Khalil et al. |
| 7,043,305 B2 | 5/2006 | KenKnight et al. |
| 7,052,472 B1 | 5/2006 | Miller et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,074,307 B2 | 7/2006 | Simpson et al. |
| 7,076,300 B1 | 7/2006 | Kroll et al. |
| 7,081,195 B2 | 7/2006 | Simpson et al. |
| 7,082,334 B2 | 7/2006 | Boute et al. |
| 7,092,891 B2 | 8/2006 | Maus et al. |
| 7,096,064 B2 | 8/2006 | Deno et al. |
| 7,098,803 B2 | 8/2006 | Mann et al. |
| 7,103,412 B1 | 9/2006 | Kroll |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,125,382 B2 | 10/2006 | Zhou et al. |
| 7,134,999 B2 | 11/2006 | Brauker et al. |
| 7,136,689 B2 | 11/2006 | Shults et al. |
| 7,142,911 B2 | 11/2006 | Boileau et al. |
| 7,153,265 B2 | 12/2006 | Vachon |
| 7,167,818 B2 | 1/2007 | Brown |
| 7,171,274 B2 | 1/2007 | Starkweather et al. |
| 7,183,102 B2 | 2/2007 | Monfre et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,225,535 B2 | 6/2007 | Feldman et al. |
| 7,226,978 B2 | 6/2007 | Tapsak et al. |
| 7,228,182 B2 | 6/2007 | Healy et al. |
| 7,237,712 B2 | 7/2007 | DeRocco et al. |
| 7,258,673 B2 | 8/2007 | Racchini et al. |
| 7,267,665 B2 | 9/2007 | Steil et al. |
| 7,272,436 B2 | 9/2007 | Gill et al. |
| 7,276,029 B2 | 10/2007 | Goode, Jr. et al. |
| 7,278,983 B2 | 10/2007 | Ireland et al. |
| 7,295,867 B2 | 11/2007 | Berner et al. |
| 7,297,114 B2 | 11/2007 | Gill et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,318,816 B2 | 1/2008 | Bobroff et al. |
| 7,324,850 B2 | 1/2008 | Persen et al. |
| 7,335,294 B2 | 2/2008 | Heller et al. |
| 7,347,819 B2 | 3/2008 | Lebel et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,384,397 B2 | 6/2008 | Zhang et al. |
| 7,387,010 B2 | 6/2008 | Sunshine et al. |
| 7,399,277 B2 | 7/2008 | Saidara et al. |
| 7,402,153 B2 | 7/2008 | Steil et al. |
| 7,404,796 B2 | 7/2008 | Ginsberg |
| 7,419,573 B2 | 9/2008 | Gundel |
| 7,424,318 B2 | 9/2008 | Brister et al. |
| 7,460,898 B2 | 12/2008 | Brister et al. |
| 7,467,003 B2 | 12/2008 | Brister et al. |
| 7,468,125 B2 | 12/2008 | Kraft et al. |
| 7,471,972 B2 | 12/2008 | Rhodes et al. |
| 7,474,992 B2 | 1/2009 | Ariyur |
| 7,492,254 B2 | 2/2009 | Bandy et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,502,644 B2 | 3/2009 | Gill et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,524,287 B2 | 4/2009 | Bharmi |
| 7,547,281 B2 | 6/2009 | Hayes et al. |
| 7,565,197 B2 | 7/2009 | Haubrich et al. |
| 7,569,030 B2 | 8/2009 | Lebel et al. |
| 7,574,266 B2 | 8/2009 | Dudding et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,613,491 B2 | 11/2009 | Boock et al. |

(56) References Cited

U.S. PATENT DOCUMENTS

| | | |
|---|---|---|
| 7,615,007 B2 | 11/2009 | Shults et al. |
| 7,618,369 B2 | 11/2009 | Hayter et al. |
| 7,620,438 B2 | 11/2009 | He |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,659,823 B1 | 2/2010 | Killian et al. |
| 7,668,596 B2 | 2/2010 | Von Arx et al. |
| 7,699,775 B2 | 4/2010 | Desai et al. |
| 7,699,964 B2 | 4/2010 | Feldman et al. |
| 7,711,493 B2 | 5/2010 | Bartkowiak et al. |
| 7,736,310 B2 | 6/2010 | Taub et al. |
| 7,741,734 B2 | 6/2010 | Joannopoulos et al. |
| 7,751,864 B2 | 7/2010 | Buck, Jr. |
| 7,766,829 B2 | 8/2010 | Sloan et al. |
| 7,771,352 B2 | 8/2010 | Shults et al. |
| 7,774,145 B2 | 8/2010 | Bruaker et al. |
| 7,778,680 B2 | 8/2010 | Goode, Jr. et al. |
| 7,779,332 B2 | 8/2010 | Karr et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,826,981 B2 | 11/2010 | Goode, Jr. et al. |
| 7,831,310 B2 | 11/2010 | Lebel et al. |
| 7,857,760 B2 | 12/2010 | Brister et al. |
| 7,860,574 B2 | 12/2010 | Von Arx et al. |
| 7,866,026 B1 | 1/2011 | Wang et al. |
| 7,882,611 B2 | 2/2011 | Shah et al. |
| 7,885,697 B2 | 2/2011 | Brister et al. |
| 7,889,069 B2 | 2/2011 | Fifolt et al. |
| 7,899,511 B2 | 3/2011 | Shults et al. |
| 7,905,833 B2 | 3/2011 | Brister et al. |
| 7,912,674 B2 | 3/2011 | Killoren Clark et al. |
| 7,914,450 B2 | 3/2011 | Goode, Jr. et al. |
| 7,916,013 B2 | 3/2011 | Stevenson |
| 7,938,797 B2 | 5/2011 | Estes |
| 7,946,984 B2 | 5/2011 | Brister et al. |
| 7,955,258 B2 | 6/2011 | Goscha et al. |
| 7,970,448 B2 | 6/2011 | Shults et al. |
| 7,974,672 B2 | 7/2011 | Shults et al. |
| 7,999,674 B2 | 8/2011 | Kamen |
| 8,060,173 B2 | 11/2011 | Goode, Jr. et al. |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,111,042 B2 | 2/2012 | Bennett |
| 8,115,488 B2 | 2/2012 | McDowell |
| 8,116,681 B2 | 2/2012 | Baarman |
| 8,116,683 B2 | 2/2012 | Baarman |
| 8,116,837 B2 | 2/2012 | Huang |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Dicks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,140,312 B2 | 3/2012 | Hayter et al. |
| 8,150,321 B2 | 4/2012 | Winter et al. |
| 8,150,516 B2 | 4/2012 | Levine et al. |
| 8,160,900 B2 | 4/2012 | Taub et al. |
| 8,170,803 B2 | 5/2012 | Kamath et al. |
| 8,179,266 B2 | 5/2012 | Hermle |
| 8,211,016 B2 | 7/2012 | Budiman |
| 8,216,137 B2 | 7/2012 | Budiman |
| 8,216,138 B1 | 7/2012 | McGarraugh et al. |
| 8,224,415 B2 | 7/2012 | Budiman et al. |
| 8,239,166 B2 | 8/2012 | Hayter et al. |
| 8,255,026 B1 | 8/2012 | Al-Ali |
| 8,282,549 B2 | 10/2012 | Brauker et al. |
| 8,376,945 B2 | 2/2013 | Hayter et al. |
| 8,444,560 B2 | 5/2013 | Hayter et al. |
| 8,457,703 B2 | 6/2013 | Al-Ali |
| 8,484,005 B2 | 7/2013 | Hayter et al. |
| 8,532,935 B2 | 9/2013 | Budiman |
| 8,543,354 B2 | 9/2013 | Luo et al. |
| 8,571,808 B2 | 10/2013 | Hayter |
| 8,612,163 B2 | 12/2013 | Hayter et al. |
| 8,657,746 B2 | 2/2014 | Roy |
| 8,682,615 B2 | 3/2014 | Hayter et al. |
| 9,060,719 B2 | 6/2015 | Hayter et al. |
| 9,113,828 B2 | 8/2015 | Budiman |
| 9,317,657 B2 * | 4/2016 | Breton .............. A61B 5/0002 |
| 9,398,872 B2 | 7/2016 | Hayter et al. |
| 9,408,566 B2 | 8/2016 | Hayter et al. |
| 9,483,608 B2 | 11/2016 | Hayter et al. |
| 9,558,325 B2 | 1/2017 | Hayter et al. |
| 2001/0041831 A1 | 11/2001 | Starkweather et al. |
| 2002/0016534 A1 | 2/2002 | Trepagnier et al. |
| 2002/0019022 A1 | 2/2002 | Dunn et al. |
| 2002/0042090 A1 | 4/2002 | Heller et al. |
| 2002/0065454 A1 | 5/2002 | Lebel et al. |
| 2002/0068860 A1 | 6/2002 | Clark |
| 2002/0072784 A1 | 6/2002 | Sheppard et al. |
| 2002/0103499 A1 | 8/2002 | Perez et al. |
| 2002/0106709 A1 | 8/2002 | Potts et al. |
| 2002/0120186 A1 | 8/2002 | Keimel |
| 2002/0128594 A1 | 9/2002 | Das et al. |
| 2002/0143266 A1 | 10/2002 | Bock |
| 2002/0143372 A1 | 10/2002 | Snell et al. |
| 2002/0161288 A1 | 10/2002 | Shin et al. |
| 2002/0169635 A1 | 11/2002 | Shillingburg |
| 2002/0193679 A1 | 12/2002 | Malave et al. |
| 2003/0004403 A1 | 1/2003 | Drinan et al. |
| 2003/0023317 A1 | 1/2003 | Brauker et al. |
| 2003/0023461 A1 | 1/2003 | Quintanilla et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0050546 A1 | 3/2003 | Desai et al. |
| 2003/0054428 A1 | 3/2003 | Monfre et al. |
| 2003/0065308 A1 | 4/2003 | Lebel et al. |
| 2003/0100821 A1 | 5/2003 | Heller et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199744 A1 | 10/2003 | Buse et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2003/0235817 A1 | 12/2003 | Bartkowiak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0024553 A1 | 2/2004 | Monfre et al. |

(56) References Cited

U.S. PATENT DOCUMENTS

| | | |
|---|---|---|
| 2004/0039298 A1 | 2/2004 | Abreu |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0064068 A1 | 4/2004 | DeNuzzio et al. |
| 2004/0077962 A1 | 4/2004 | Kroll |
| 2004/0078065 A1 | 4/2004 | Kroll |
| 2004/0093167 A1 | 5/2004 | Braig et al. |
| 2004/0099529 A1 | 5/2004 | Mao et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0135684 A1 | 7/2004 | Steinthal et al. |
| 2004/0138588 A1 | 7/2004 | Saikley et al. |
| 2004/0138716 A1 | 7/2004 | Kon et al. |
| 2004/0142403 A1 | 7/2004 | Hetzel et al. |
| 2004/0146909 A1 | 7/2004 | Duong et al. |
| 2004/0152622 A1 | 8/2004 | Keith et al. |
| 2004/0162678 A1 | 8/2004 | Hetzel et al. |
| 2004/0167801 A1 | 8/2004 | Say et al. |
| 2004/0171921 A1 | 9/2004 | Say et al. |
| 2004/0172307 A1 | 9/2004 | Gruber |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204687 A1 | 10/2004 | Mogensen et al. |
| 2004/0208780 A1 | 10/2004 | Faries, Jr. et al. |
| 2004/0225338 A1 | 11/2004 | Lebel et al. |
| 2004/0236200 A1 | 11/2004 | Say et al. |
| 2004/0249253 A1 | 12/2004 | Racchini et al. |
| 2004/0249420 A1 | 12/2004 | Olson et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0263354 A1 | 12/2004 | Mann et al. |
| 2004/0267300 A1 | 12/2004 | Mace |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0010087 A1 | 1/2005 | Banet et al. |
| 2005/0010269 A1 | 1/2005 | Lebel et al. |
| 2005/0016276 A1 | 1/2005 | Guan et al. |
| 2005/0017864 A1 | 1/2005 | Tsoukalis |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0049179 A1 | 3/2005 | Davidson et al. |
| 2005/0049473 A1 | 3/2005 | Desai et al. |
| 2005/0070774 A1 | 3/2005 | Addison et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0112169 A1 | 5/2005 | Brauker et al. |
| 2005/0113653 A1 | 5/2005 | Fox et al. |
| 2005/0114068 A1 | 5/2005 | Chey et al. |
| 2005/0115832 A1 | 6/2005 | Simpson et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0154271 A1 | 7/2005 | Rasdal et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0196821 A1 | 9/2005 | Monfre et al. |
| 2005/0199494 A1 | 9/2005 | Say et al. |
| 2005/0203360 A1 | 9/2005 | Brauker et al. |
| 2005/0214892 A1 | 9/2005 | Kovatchev et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0277164 A1 | 12/2005 | Drucker et al. |
| 2005/0277912 A1 | 12/2005 | John |
| 2005/0287620 A1 | 12/2005 | Heller et al. |
| 2005/0288725 A1 | 12/2005 | Hettrick et al. |
| 2006/0001538 A1 | 1/2006 | Kraft et al. |
| 2006/0004270 A1 | 1/2006 | Bedard et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025662 A1 | 2/2006 | Buse et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0058588 A1 | 3/2006 | Zdeblick |
| 2006/0091006 A1 | 5/2006 | Wang et al. |
| 2006/0142651 A1 | 6/2006 | Brister et al. |
| 2006/0155180 A1 | 7/2006 | Brister et al. |
| 2006/0166629 A1 | 7/2006 | Reggiardo |
| 2006/0167365 A1 | 7/2006 | Bhalini |
| 2006/0167517 A1 | 7/2006 | Gill et al. |
| 2006/0167518 A1 | 7/2006 | Gill et al. |
| 2006/0167519 A1 | 7/2006 | Gill et al. |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189851 A1 | 8/2006 | Tvig et al. |
| 2006/0189863 A1 | 8/2006 | Peyser et al. |
| 2006/0193375 A1 | 8/2006 | Lee |
| 2006/0222566 A1 | 10/2006 | Brauker et al. |
| 2006/0224109 A1 | 10/2006 | Steil et al. |
| 2006/0226985 A1 | 10/2006 | Goodnow et al. |
| 2006/0229512 A1 | 10/2006 | Petisce et al. |
| 2006/0247508 A1 | 11/2006 | Fennell |
| 2006/0247685 A1 | 11/2006 | Bharmi |
| 2006/0247710 A1 | 11/2006 | Goetz et al. |
| 2006/0247985 A1 | 11/2006 | Liamos et al. |
| 2006/0258929 A1 | 11/2006 | Goode et al. |
| 2006/0264785 A1 | 11/2006 | Dring et al. |
| 2006/0272652 A1 | 12/2006 | Stocker et al. |
| 2006/0281985 A1 | 12/2006 | Ward et al. |
| 2006/0287691 A1 | 12/2006 | Drew |
| 2007/0016381 A1 | 1/2007 | Kamath et al. |
| 2007/0027381 A1 | 2/2007 | Stafford |
| 2007/0032706 A1 | 2/2007 | Kamath et al. |
| 2007/0033074 A1 | 2/2007 | Nitzan et al. |
| 2007/0038044 A1 | 2/2007 | Dobbles et al. |
| 2007/0055799 A1 | 3/2007 | Koehler et al. |

(56) References Cited

U.S. PATENT DOCUMENTS

| | | |
|---|---|---|
| 2007/0056858 A1 | 3/2007 | Chen et al. |
| 2007/0060803 A1 | 3/2007 | Liljeryd et al. |
| 2007/0060814 A1 | 3/2007 | Stafford |
| 2007/0066873 A1 | 3/2007 | Kamath et al. |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0095661 A1 | 5/2007 | Wang et al. |
| 2007/0106135 A1 | 5/2007 | Sloan et al. |
| 2007/0108048 A1 | 5/2007 | Wang et al. |
| 2007/0118030 A1 | 5/2007 | Bruce et al. |
| 2007/0118405 A1 | 5/2007 | Campbell et al. |
| 2007/0124002 A1 | 5/2007 | Estes et al. |
| 2007/0129621 A1 | 6/2007 | Kellogg et al. |
| 2007/0149875 A1 | 6/2007 | Ouyang et al. |
| 2007/0156033 A1 | 7/2007 | Causey, III et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179434 A1 | 8/2007 | Weinert et al. |
| 2007/0191701 A1 | 8/2007 | Feldman et al. |
| 2007/0199818 A1 | 8/2007 | Petyt et al. |
| 2007/0202562 A1 | 8/2007 | Curry et al. |
| 2007/0203407 A1 | 8/2007 | Hoss et al. |
| 2007/0203966 A1 | 8/2007 | Brauker et al. |
| 2007/0213657 A1 | 9/2007 | Jennewine et al. |
| 2007/0227911 A1 | 10/2007 | Wang et al. |
| 2007/0232877 A1 | 10/2007 | He |
| 2007/0232878 A1 | 10/2007 | Kovatchev et al. |
| 2007/0232880 A1 | 10/2007 | Siddiqui et al. |
| 2007/0233013 A1 | 10/2007 | Schoenberg et al. |
| 2007/0235331 A1 | 10/2007 | Simpson et al. |
| 2007/0244383 A1 | 10/2007 | Talbot et al. |
| 2007/0249922 A1 | 10/2007 | Peyser et al. |
| 2007/0253021 A1 | 11/2007 | Mehta et al. |
| 2007/0255321 A1 | 11/2007 | Gerber et al. |
| 2007/0255531 A1 | 11/2007 | Drew |
| 2007/0258395 A1 | 11/2007 | Jollota et al. |
| 2007/0270672 A1 | 11/2007 | Hayter |
| 2007/0282299 A1 | 12/2007 | Hellwig |
| 2007/0285238 A1 | 12/2007 | Batra |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0012701 A1 | 1/2008 | Kass et al. |
| 2008/0017522 A1 | 1/2008 | Heller et al. |
| 2008/0018433 A1 | 1/2008 | Pitt-Pladdy |
| 2008/0021666 A1 | 1/2008 | Goode, Jr. et al. |
| 2008/0021972 A1 | 1/2008 | Huelskamp et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0064937 A1 | 3/2008 | McGarraugh et al. |
| 2008/0064943 A1 | 3/2008 | Talbot et al. |
| 2008/0066305 A1 | 3/2008 | Wang et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097289 A1 | 4/2008 | Steil et al. |
| 2008/0102441 A1 | 5/2008 | Chen et al. |
| 2008/0108942 A1 | 5/2008 | Brister et al. |
| 2008/0119703 A1 | 5/2008 | Brister et al. |
| 2008/0119705 A1 | 5/2008 | Patel et al. |
| 2008/0119708 A1 | 5/2008 | Budiman |
| 2008/0139910 A1 | 6/2008 | Mastrototaro et al. |
| 2008/0148873 A1 | 6/2008 | Wang |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0167572 A1 | 7/2008 | Stivoric et al. |
| 2008/0172205 A1 | 7/2008 | Breton et al. |
| 2008/0177149 A1 | 7/2008 | Weinert et al. |
| 2008/0177165 A1 | 7/2008 | Blomquist et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0208113 A1 | 8/2008 | Damiano et al. |
| 2008/0214910 A1 | 9/2008 | Buck |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0234943 A1 | 9/2008 | Ray et al. |
| 2008/0235469 A1 | 9/2008 | Drew |
| 2008/0242961 A1 | 10/2008 | Brister et al. |
| 2008/0242963 A1 | 10/2008 | Essenpreis et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0267823 A1 | 10/2008 | Wang et al. |
| 2008/0275313 A1 | 11/2008 | Brister et al. |
| 2008/0278332 A1 | 11/2008 | Fennel et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2008/0319279 A1 | 12/2008 | Ramsay et al. |
| 2008/0319295 A1 | 12/2008 | Bernstein et al. |
| 2008/0319296 A1 | 12/2008 | Bernstein et al. |
| 2009/0005665 A1 | 1/2009 | Hayter et al. |

(56) References Cited

U.S. PATENT DOCUMENTS

| | | |
|---|---|---|
| 2009/0005666 A1 | 1/2009 | Shin et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012376 A1 | 1/2009 | Agus |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030293 A1 | 1/2009 | Cooper et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054748 A1 | 2/2009 | Feldman et al. |
| 2009/0054749 A1 | 2/2009 | He |
| 2009/0054753 A1 | 2/2009 | Robinson et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0069649 A1 | 3/2009 | Budiman |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0099436 A1 | 4/2009 | Brister et al. |
| 2009/0105554 A1 | 4/2009 | Stahmann et al. |
| 2009/0105560 A1 | 4/2009 | Solomon |
| 2009/0105570 A1 | 4/2009 | Sloan et al. |
| 2009/0105636 A1 | 4/2009 | Hayter et al. |
| 2009/0112478 A1 | 4/2009 | Mueller, Jr. et al. |
| 2009/0112626 A1 | 4/2009 | Talbot et al. |
| 2009/0118589 A1 | 5/2009 | Ueshima et al. |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0143725 A1 | 6/2009 | Peyser et al. |
| 2009/0149728 A1 | 6/2009 | Van Antwerp et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0182517 A1 | 7/2009 | Gandhi et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0234200 A1 | 9/2009 | Husheer |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0253973 A1 | 10/2009 | Bashan et al. |
| 2009/0257911 A1 | 10/2009 | Thomas et al. |
| 2009/0267765 A1 | 10/2009 | Greene et al. |
| 2009/0281407 A1 | 11/2009 | Budiman |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0294277 A1 | 12/2009 | Thomas et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063372 A1 | 3/2010 | Potts et al. |
| 2010/0064764 A1 | 3/2010 | Hayter et al. |
| 2010/0081906 A1 | 4/2010 | Hayter et al. |
| 2010/0081909 A1 | 4/2010 | Budiman et al. |
| 2010/0081953 A1 | 4/2010 | Syeda-Mahmood et al. |
| 2010/0121167 A1 | 5/2010 | McGarraugh et al. |
| 2010/0141656 A1 | 6/2010 | Krieftewirth |
| 2010/0152561 A1 | 6/2010 | Goodnow et al. |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174266 A1 | 7/2010 | Estes |
| 2010/0190435 A1 | 7/2010 | Cook et al. |
| 2010/0191085 A1 | 7/2010 | Budiman |
| 2010/0191472 A1 | 7/2010 | Doniger et al. |
| 2010/0198034 A1 | 8/2010 | Thomas et al. |
| 2010/0198142 A1 | 8/2010 | Sloan et al. |
| 2010/0204557 A1 | 8/2010 | Kiaie et al. |
| 2010/0213057 A1 | 8/2010 | Feldman et al. |
| 2010/0230285 A1 | 9/2010 | Hoss et al. |
| 2010/0234710 A1 | 9/2010 | Budiman et al. |
| 2010/0261987 A1 | 10/2010 | Kamath et al. |
| 2010/0265073 A1 | 10/2010 | Harper et al. |
| 2010/0274515 A1 | 10/2010 | Hoss et al. |
| 2010/0277342 A1 | 11/2010 | Sicurello et al. |
| 2010/0280441 A1 | 11/2010 | Willinska et al. |
| 2010/0280782 A1 | 11/2010 | Harper et al. |
| 2010/0312176 A1 | 12/2010 | Lauer et al. |
| 2010/0313105 A1 | 12/2010 | Nekoomaram et al. |
| 2010/0317952 A1 | 12/2010 | Budiman et al. |
| 2010/0324392 A1 | 12/2010 | Yee et al. |
| 2010/0326842 A1 | 12/2010 | Mazza et al. |
| 2011/0004276 A1 | 1/2011 | Blair et al. |
| 2011/0021889 A1 | 1/2011 | Hoss et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0029247 A1 | 2/2011 | Kalathil |
| 2011/0040163 A1 | 2/2011 | Telson et al. |

(56) References Cited

U.S. PATENT DOCUMENTS

| | | | |
|---|---|---|---|
| 2011/0060530 A1 | 3/2011 | Fennell | |
| 2011/0077490 A1 | 3/2011 | Simpson et al. | |
| 2011/0077494 A1 | 3/2011 | Doniger et al. | |
| 2011/0081726 A1 | 4/2011 | Berman et al. | |
| 2011/0082484 A1 | 4/2011 | Saravia et al. | |
| 2011/0105873 A1 | 5/2011 | Feldman et al. | |
| 2011/0106126 A1 | 5/2011 | Love et al. | |
| 2011/0112696 A1 | 5/2011 | Yodfat et al. | |
| 2011/0148905 A1 | 6/2011 | Simmons et al. | |
| 2011/0152637 A1 | 6/2011 | Kateraas et al. | |
| 2011/0184268 A1 | 7/2011 | Taub | |
| 2011/0190603 A1 | 8/2011 | Stafford | |
| 2011/0191044 A1 | 8/2011 | Stafford | |
| 2011/0193704 A1 | 8/2011 | Harper et al. | |
| 2011/0208027 A1 | 8/2011 | Wagner et al. | |
| 2011/0208155 A1 | 8/2011 | Paleint et al. | |
| 2011/0213225 A1 | 9/2011 | Bernstein | |
| 2011/0224523 A1 | 9/2011 | Budiman | |
| 2011/0257495 A1 | 10/2011 | Hoss et al. | |
| 2011/0257895 A1 | 10/2011 | Brauker et al. | |
| 2011/0263958 A1 | 10/2011 | Brauker et al. | |
| 2011/0288574 A1 | 11/2011 | Curry et al. | |
| 2011/0319729 A1 | 12/2011 | Donnay et al. | |
| 2011/0320130 A1 | 12/2011 | Valdes et al. | |
| 2011/0320167 A1 | 12/2011 | Budiman | |
| 2012/0010642 A1 | 1/2012 | Lee et al. | |
| 2012/0078071 A1 | 3/2012 | Bohm et al. | |
| 2012/0108931 A1 | 5/2012 | Taub | |
| 2012/0108934 A1 | 5/2012 | Valdes et al. | |
| 2012/0165626 A1 | 6/2012 | Irina et al. | |
| 2012/0165640 A1 | 6/2012 | Galley et al. | |
| 2012/0173200 A1 | 7/2012 | Breton et al. | |
| 2012/0209099 A1 | 8/2012 | Ljuhs et al. | |
| 2012/0215462 A1 | 8/2012 | Goode et al. | |
| 2012/0245447 A1 | 9/2012 | Karan et al. | |
| 2012/0277565 A1 | 11/2012 | Budiman | |
| 2012/0283542 A1 | 11/2012 | McGarraugh | |
| 2013/0035575 A1 | 2/2013 | Mayou et al. | |
| 2013/0137953 A1 | 5/2013 | Harper et al. | |
| 2013/0184547 A1 | 7/2013 | Taub et al. | |
| 2013/0231541 A1 | 9/2013 | Hayter et al. | |
| 2013/0324823 A1 | 12/2013 | Koski et al. | |
| 2014/0005499 A1 | 1/2014 | Catt et al. | |
| 2014/0046160 A1 | 2/2014 | Terashima et al. | |
| 2014/0088392 A1 | 3/2014 | Bernstein et al. | |
| 2014/0121480 A1 | 5/2014 | Budiman et al. | |
| 2014/0121488 A1 | 5/2014 | Budiman | |
| 2014/0182350 A1* | 7/2014 | Bhavaraju | G01M 99/008 73/1.02 |
| 2014/0221966 A1 | 8/2014 | Buckingham et al. | |
| 2015/0216456 A1 | 8/2015 | Budiman | |
| 2015/0241407 A1 | 8/2015 | Ou et al. | |
| 2015/0366510 A1 | 12/2015 | Budiman | |

FOREIGN PATENT DOCUMENTS

| | | |
|---|---|---|
| EP | 0320109 | 6/1989 |
| EP | 0353328 | 2/1990 |
| EP | 0390390 | 10/1990 |
| EP | 0396788 | 11/1990 |
| EP | 0472411 | 2/1992 |
| EP | 0286118 | 1/1995 |
| EP | 0867146 | 9/1998 |
| EP | 1048264 | 11/2000 |
| EP | 1419731 | 5/2004 |
| EP | 0939602 | 9/2004 |
| EP | 1850909 | 4/2010 |
| EP | 1677668 | 7/2010 |
| WO | WO-1996/025089 | 8/1996 |
| WO | WO-1996/035370 | 11/1996 |
| WO | WO-1997/015227 | 5/1997 |
| WO | WO-2000/049940 | 8/2000 |
| WO | WO-2000/059370 | 10/2000 |
| WO | WO-2000/074753 | 12/2000 |
| WO | WO-2001/052935 | 7/2001 |
| WO | WO-2001/054753 | 8/2001 |
| WO | WO-2002/016905 | 2/2002 |
| WO | WO-2003/076893 | 9/2003 |
| WO | WO-2003/082091 | 10/2003 |
| WO | WO-2004/060455 | 7/2004 |
| WO | WO-2005/010756 | 2/2005 |
| WO | WO-2005/065542 | 7/2005 |
| WO | WO-2006/024671 | 3/2006 |
| WO | WO-2006/081336 | 8/2006 |
| WO | WO-2006/085087 | 8/2006 |
| WO | WO-2007/097754 | 8/2007 |
| WO | WO-2008/086541 | 7/2008 |
| WO | WO-2010/022387 | 2/2010 |
| WO | WO-2012/108939 | 8/2012 |

OTHER PUBLICATIONS

Arnold, M. A., et al., "Selectivity Assessment of Noninvasive Glucose Measurements Based on Analysis of Multivariate Calibration Vectors", *Journal of Diabetes Science and Technology*, vol. 1, No. 4, 2007, pp. 454-462.

Eren-Oruklu, M., et al., "Estimation of Future Glucose Concentrations with Subject-Specific Recursive Linear Models", *Diabetes Technology & Therapeutics* vol. 11(4), 2009, pp. 243-253.

PCT Application No. PCT/US2014/026845, International Search Report and Written Opinion of the International Searching Authority dated Aug. 8, 2014.

Armour, J. C., et al., "Application of Chronic Intravascular Blood Glucose Sensor in Dogs", *Diabetes*, vol. 39, 1990, pp. 1519-1526.

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Boyne, M. S., et al., "Timing of Changes in Interstitial and Venous Blood Glucose Measured With a Continuous Subcutaneous Glucose Sensor", *Diabetes*, vol. 52, Nov. 2003, pp. 2790-2794.

Bremer, T. M., et al., "Benchmark Data from the Literature for Evaluation of New Glucose Sensing Technologies", *Diabetes Technology & Therapeutics*, vol. 3, No. 3, 2001, pp. 409-418.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Detelinination of Glucose", *Analytical Chemistry*, vol. 56, No. 4, 1984, 667-671.

Cheyne, E. H., et al., "Performance of a Continuous Glucose Monitoring System During Controlled Hypoglycaemia in Healthy Volunteers", *Diabetes Technology & Therapeutics*, vol. 4, No. 5, 2002, pp. 607-613.

Choleau, C., et al., "Calibration of a Subcutaneous Amperometric Glucose Sensor Implanted for 7 Days in Diabetic Patients Part 2. Superiority of the One-Point Calibration Method", *Biosensors and Bioelectronics*, vol. 17, No. 8, 2002, pp. 647-654.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Diabetes Control and Complications Trial Research Group, "The Effect of Intensive Treatment of Diabetes on the Development and Progression of Long-Term Complications in Insulin-Dependent Diabetes Mellitus," *New England J. Med.* vol. 329, 1993, pp. 977-986.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glu-

(56) References Cited

OTHER PUBLICATIONS cose Change", *Abbott Diabetes Care, Inc. Freestyle Navigator Continuous Glucose Monitor Pamphlet*, 2004.
Georgescu, B., et al., "Real-Time Multimodel Tracking of Myocardium in Echocardiography Using Robust Infamiation Fusion", *Medical Image Computing and Computer-Assisted Intervention*, 2004, pp. 777-785.
Goldman, J. M., et al., "Masimo Signal Extraction Pulse Oximetry", *Journal of Clinical Monitoring and Computing*, vol. 16, No. 7, 2000, pp. 475-483.
Guerci, B., et al., "Clinical Perfoimance of CGMS in Type 1 Diabetic Patients Treated by Continuous Subcutaneous Insulin Infusion Using Insulin Analogs", *Diabetes Care*, vol. 26, 2003, pp. 582-589.
Isermann, R., "Supervision, Fault-Detection and Fault-Diagnosis Methods—An Introduction", *Control Engineering Practice*, vol. 5, No. 5, 1997, pp. 639-652.
Isermann, R., et al., "Trends in the Application of Model-Based Fault Detection and Diagnosis of Technical Processes", *Control Engineering Practice*, vol. 5, No. 5, 1997, pp. 709-719.
Johnson, P. C., "Peripheral Circulation", *John Wiley & Sons*, 1978, pp. 198.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm" *Diabetes Care*, vol. 24, No. 7, 2001, pp. 1303-1304.
Kaplan, S. M., "Wiley Electrical and Electronics Engineering Dictionary", *IEEE Press*, 2004, pp. 141, 142, 548, 549.
Kovatchev, B. P., et al., "Evaluating the Accuracy of Continuous Glucose-Monitoring Sensors", *Diabetes Care*, vol. 27, No. 8, 2004, pp. 1922-1928.
Kuure-Kinsey, M., et al., "A Dual-Rate Kalman Filter for Continuous Glucose Monitoring", *Proceedings of the 28th IEEE, EMBS Annual International Conference, New York City*, 2006, pp. 63-66.
Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.
Lortz, J., et al., "What is Bluetooth? We Explain The Newest Short-Range Connectivity Technology", *Smart Computing Learning Series, Wireless Computing*, vol. 8, Issue 5, 2002, pp. 72-74.
Maher, "A Method for Extrapolation of Missing Digital Audio Data", *Preprints of Papers Presented at the AES Convention*, 1993, pp. 1-19.
Maher, "Audio Enhancement using Nonlinear Time-Frequency Filtering", *AES 26th International Conference*, 2005, pp. 1-9.
Malin, S. F., et al., "Noninvasive Prediction of Glucose by Near-Infrared Diffuse Reflectance Spectoscopy", *Clinical Chemistry*, vol. 45 No. 9, 1999, pp. 1651-1658.
McGarraugh, G., et al., "Glucose Measurements Using Blood Extracted from the Forearm and the Finger", *TheraSense, Inc.*, 2001, 16 Pages.
McGarraugh, G., et al., "Physiological Influences on Off-Finger Glucose Testing", *Diabetes Technology & Therapeutics*, vol. 3, No. 3, 2001, pp. 367-376.
McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.
Morbiducci, U, et al., "Improved Usability of the Minimal Model of Insulin Sensitivity Based on an Automated Approach and Genetic Algorithms for Parameter Estimation", *Clinical Science*, vol. 112, 2007, pp. 257-263.
Mougiakakou, et al., "A Real Time Simulation Model of Glucose-Insulin Metabolism for Type 1 Diabetes Patients", *Proceedings of the 2005 IEEE*, 2005, pp. 298-301.
Panteleon, A. E., et al., "The Role of the Independent Variable to Glucose Sensor Calibration", *Diabetes Technology & Therapeutics*, vol. 5, No. 3, 2003, pp. 401-410.

Parker, R., et al., "Robust H∞ Glucose Control in Diabetes Using a Physiological Model", *AIChE Journal*, vol. 46, No. 12, 2000, pp. 2537-2549.
Pickup, J., et al., "Implantable Glucose Sensors: Choosing the Appropriate Sensing Strategy", *Biosensors*, vol. 3, 1987/88, pp. 335-346.
Pickup, J., et al., "In Vivo Molecular Sensing in Diabetes Mellitus: An Implantable Glucose Sensor with Direct Electron Transfer", *Diabetologia*, vol. 32, 1989, pp. 213-217.
Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.
Quinn, C. P., et al., "Kinetics of Glucose Delivery to Subcutaneous Tissue in Rats Measured with 0.3-mm Amperometric Microsensors", *The American Physiological Society*, 1995, E155-E161.
Roe, J. N., et al., "Bloodless Glucose Measurements", *Critical Review in Therapeutic Drug Carrier Systems*, vol. 15, Issue 3, 1998, pp. 199-241.
Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.
Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.
Salehi, C., et al., "A Telemetry-Instrumentation System for Long-Term Implantable Glucose and Oxygen Sensors", *Analytical Letters*, vol. 29, No. 13, 1996, pp. 2289-2308.
Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.
Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.
Shichiri, M., et al., "Glycaemic Control in Pancreatectomized Dogs with a Wearable Artificial Endocrine Pancreas", *Diabetologia*, vol. 24, 1983, pp. 179-184.
Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.
Shichiri, M., et al., "Membrane Design for Extending the Long-Life of an Implantable Glucose Sensor", *Diabetes Nutrition and Metabolism*, vol. 2, 1989, pp. 309-313.
Shichiri, M., et al., "Needle-type Glucose Sensor for Wearable Artificial Endocrine Pancreas", *Implantable Sensors for Closed-Loop Prosthetic Systems, Chapter 15*, 1985, pp. 197-210.
Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.
Shichiri, M., et al., "Wearable Artificial Endocrine Pancreas With Needle-Type Glucose Sensor", *The Lancet*, 1982, pp. 1129-1131.
Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.
Sternberg, R., et al., "Study and Development of Multilayer Needle-Type Enzyme-Based Glucose Microsensors", *Biosensors*, vol. 4, 1988, pp. 27-40.
Thompson, M., et al., "In Vivo Probes: Problems and Perspectives", *Clinical Biochemistry*, vol. 19, 1986, pp. 255-261.
Turner, A., et al., "Diabetes Mellitus: Biosensors for Research and Management", *Biosensors*, vol. 1, 1985, pp. 85-115.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring, Chapter 4*, 1997, pp. 117-137.
Velho, G., et al., "Strategies for Calibrating a Subcutaneous Glucose Sensor", *Biomedica Biochimica Acta*, vol. 48, 1989, pp. 957-964.

(56) References Cited

OTHER PUBLICATIONS

Whipple, G., "Low Residual Noise Speech Enhancement Utilizing Time-Frequency", *Proceedings of the International Conference on Acoustics, Speech, and Signal Processing*, vol. 19, 1994, pp. 15-18.

Wilson, G. S., et al., "Progress Toward the Development of an Implantable Sensor for Glucose", *Clinical Chemistry*, vol. 38, No. 9, 1992, pp. 1613-1617.

Wolfe, P. J., et al., "Interpolation of Missing Data Values for Audio Signal Restoration Using a Gabor Regression Model", *2005 IEEE International Conference on Acoustics, Speech, and Signal Processing*, vol. 5, 2005, pp. 517-520.

Dassau, E., et al., "Detection of a Meal Using Continuous Glucose Monitoring", *Emerging Treatments and Technologies*, vol. 31, No. 2, Feb. 2008, pp. 295-300.

Hovorka, R., et al., "Nonlinear Model Predictive Control of Glucose Concentration in Subjects with Type 1 Diabetes", *Physiological Measurement*, vol. 55, Jul. 2004, pp. 905-920.

Hyunjin, L., et al., "A Closed-Loop Artificial Pancreas Using Model Predictive Control and a Sliding Meal Size Estimator", *Journal of Diabetes Science and Technology*, vol. 3, Issue 5, Sep. 2009, pp. 1082-1090.

Kovatchev, B. P., et al., "Graphical and Numerical Evaluation of Continuous Glucose Sensing Time Lag", *Diabetes Technology & Therapeutics*, vol. 11, No. 3, Feb. 2009, pp. 139-143.

Steil, G. M., et al., "Closed-Loop Insulin Delivery—the Path of Physiological Glucose Control", *Advanced Drug Delivery Reviews*, vol. 56, 2004, pp. 125-144.

Steil, G. M., et al., "Determination of Plasma Glucose During Rapid Glucose Excursions with a Subcutaneous Glucose Sensor", *Diabetes Technology & Therapeutics*, vol. 5, No. 1, 2003, pp. 27-31.

\* cited by examiner

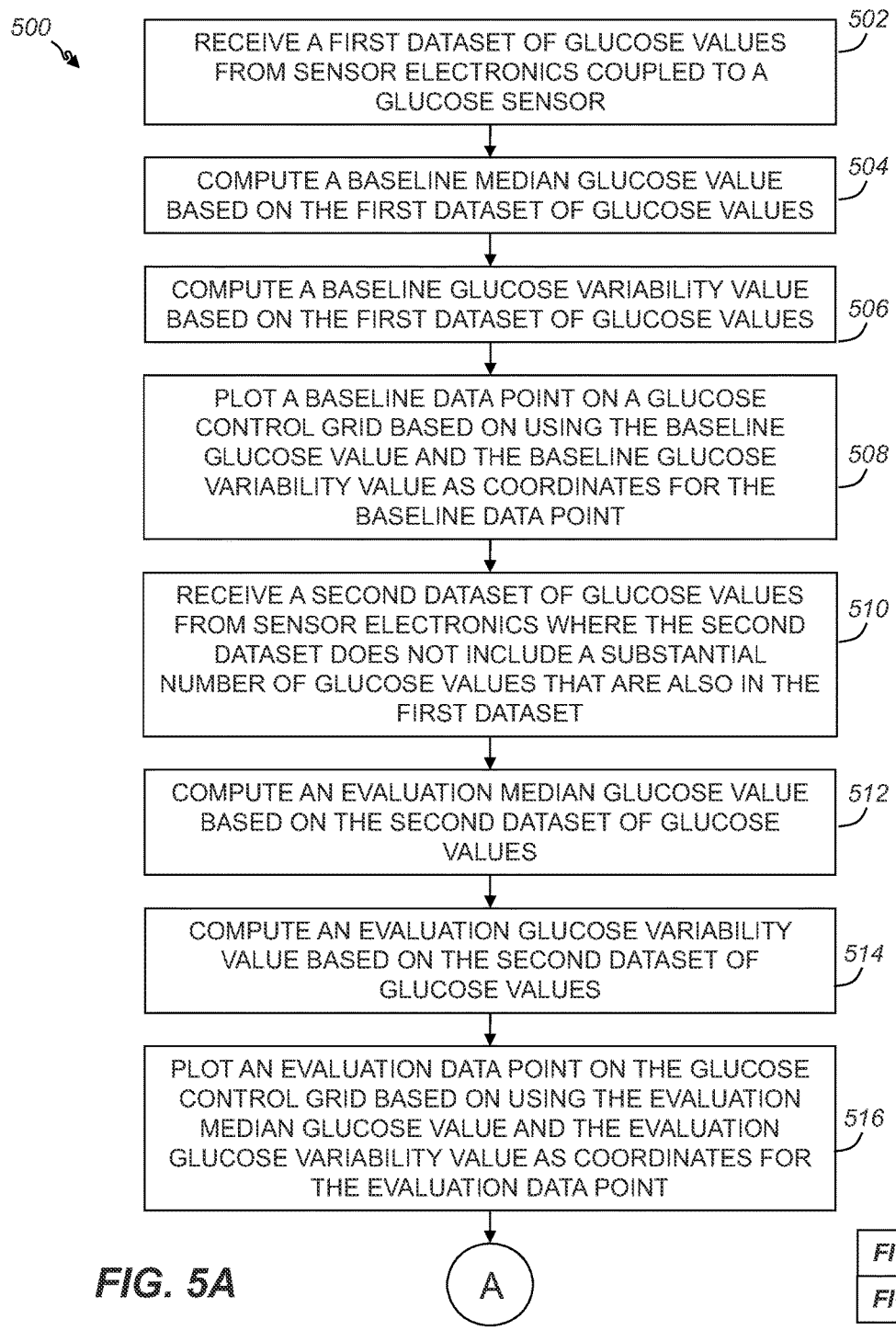

SENSOR FAULT DETECTION USING ANALYTE SENSOR DATA PATTERN COMPARISON

CROSS-REFERENCE TO RELATED APPLICATIONS

This national stage patent application under 35 U.S.C. § 371 claims priority to PCT Application No. PCT/US2014/026845 filed Mar. 13, 2014, which claims priority to U.S. Provisional Application No. 61/794,793 filed Mar. 15, 2013, entitled "Sensor Fault Detection Using Analyte Sensor Data Pattern Comparison," the disclosures of each of which are incorporated herein by reference in their entirety for all purposes.

BACKGROUND

The detection of the concentration level of glucose or other analytes in certain individuals may be vitally important to their health. For example, the monitoring of glucose levels is particularly important to individuals with diabetes or pre-diabetes. People with diabetes may need to monitor their glucose levels to determine when medication (e.g., insulin) is needed to reduce their glucose levels or when additional glucose is needed.

Devices have been developed for automated in vivo monitoring of analyte time series characteristics, such as glucose levels, in bodily fluids such as in the blood stream or in interstitial fluid. Some of these analyte level measuring devices are configured so that at least a portion of a sensor of an on-body device is positioned below a skin surface of a user, e.g., in a blood vessel or in the subcutaneous tissue of a user. As used herein, the term analyte monitoring system is used to refer to any type of in vivo monitoring system that uses a sensor disposed with at least a subcutaneous portion to measure and store sensor data representative of analyte concentration levels automatically over time. Analyte monitoring systems include both (1) systems such as continuous glucose monitors (CGMs) which transmit sensor data continuously or at regular time intervals (e.g., once per minute) to a processor/display unit and (2) systems that transfer stored sensor data in one or more batches in response to a prompt or request signal from a processor/display unit (e.g., based on an activation action and/or proximity using, for example, a near field communications protocol).

In some cases, analyte monitoring systems have been found to occasionally provide false readings due to one or more error conditions. In such instances, the analyte monitoring systems maybe described as operating in a fault mode. End of sensor life and early signal attenuation (ESA) are two examples of fault modes where false readings may occur. A decaying sensor signal due to sensor removal, patch adhesive issues, and depleted sensing chemistry are examples of causes of false readings at the end of a sensor's life. Prior art methods of detecting fault modes typically rely on in vivo calibration that compares the sensor's output with one or more in vitro reference glucose readings. Using several in vitro reference glucose readings, both the calibration factor and fault modes such as end of sensor life and ESA can be determined/detected. However, using in vitro reference glucose readings typically requires user interaction, uncomfortable "finger stick" blood samples, a supply of relatively costly test strips, and a meter that can read the test strips. Thus, what is needed are systems, methods and apparatus that do not rely on in vitro reference glucose readings to detect fault modes such as end of sensor life and ESA.

SUMMARY

The present disclosure provides systems, methods, and apparatus that allow a user (e.g., a health care provider, patient, etc.) to analyze a collection of analyte monitoring system sensor data to identify or detect sensor faults. Some embodiments of the present disclosure include computer-implemented methods of identifying sensor fault modes using analyte monitoring system sensor data. The methods include receiving first and second datasets of glucose values from sensor electronics operatively coupled to transcutaneously positioned glucose sensors, computing a baseline median glucose value and a baseline glucose variability value based on the first dataset, storing a baseline data point, computing an evaluation median glucose value and an evaluation glucose variability value based on the second dataset of glucose values, storing an evaluation data point, computing a magnitude of a vector that extends between the baseline data point and the evaluation data point, computing a component of the magnitude of the vector that is parallel to a hypoglycemia risk contour line, comparing the component to a predefined threshold value, and displaying an indication that a sensor fault has been detected if the component is greater than a threshold.

Embodiments of the present disclosure also include a computer system and a computer program product for identifying sensor fault modes using analyte monitoring system sensor data. Numerous other aspects and embodiments are provided. Other features and aspects of the present disclosure will become more fully apparent from the following detailed description, the appended claims, and the accompanying drawings.

BRIEF DESCRIPTION OF THE DRAWINGS

The accompanying drawings, which are incorporated herein, form part of the specification. Together with this written description, the drawings further serve to explain the principles of, and to enable a person skilled in the relevant arts, to make and use the present disclosure.

FIGS. 5A and 5B depict a flowchart illustrating an example method in accordance with some embodiments of the present disclosure.

DETAILED DESCRIPTION

Figure 1:
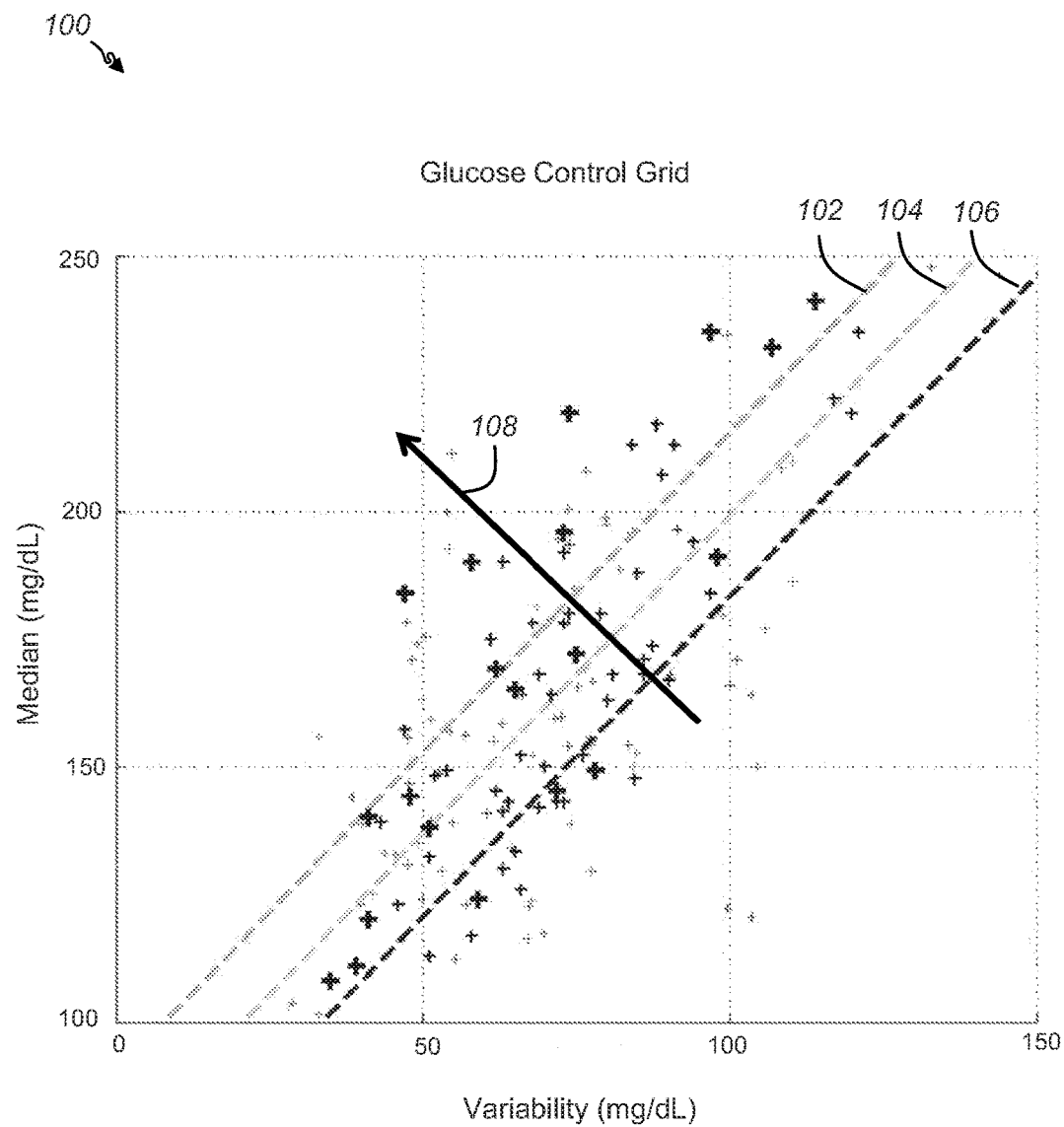
FIG. 1 depicts an example control grid in accordance with some embodiments of the present disclosure.

Before the embodiments of the present disclosure are described, it is to be understood that this invention is not limited to particular embodiments described, as such may, of course, vary. It is also to be understood that the terminology used herein is for the purpose of describing particular embodiments only, and is not intended to be limiting, since the scope of the embodiments of the invention will be limited only by the appended claims.

The present disclosure provides systems, methods, and apparatus to identify sensor fault modes using sensor data from an analyte monitoring system, such as, for example, any type of in vivo monitoring system that uses a sensor disposed with at least a subcutaneous portion to measure and store sensor data representative of analyte concentration levels automatically over time. Analyte monitoring systems may include CGMs which are programmed to transmit sensor data according to a predetermined transmission schedule, continuously, or at regular time intervals to a processor/display unit and systems that transfer stored sensor data in one or more batches in response to a request from a processor/display unit, i.e., not according to a predetermined transmission schedule. Without requiring a patient to provide blood samples for in vitro reference glucose readings, the present disclosure is operable to identify sensor faults from data from an in vivo analyte sensor.

According to some embodiments of the present disclosure, a dataset representative of a patient's monitored analyte concentration level (herein referred to as "sensor data") over time is received from sensor electronics operatively coupled to an analyte sensor in fluid contact with interstitial fluid. The measurements, especially those of the patient's analyte concentration level, are characterized by a pair of metrics. This pair provides a representation of the static and dynamic level of analyte control over a window of time. There are paired values that are physiologically feasible, and there are those that are very unlikely to be physiologically feasible. In addition, when comparing paired values from one window of time against another, the change in the quantities may or may not be physiologically feasible. The approach described herein identifies value pairs on a given measurement window and/or changes in value pairs among several measurement windows to detect non physiological changes indicative of a sensor fault. A metric for static analyte state is the median value of the sensor data. A metric for dynamic analyte state is the difference between the median and the tenth percentile values of the same sensor data, referred to herein as a variability value.

When sensor data obtained over a window of time is first obtained, a baseline pair can be calculated. A baseline median or average analyte value and a baseline analyte variability value are computed from this dataset. These baseline values are used as coordinates to plot a baseline data point on an analyte control grid. Once a second, subsequent dataset is received from the sensor electronics that does not include a significant number of analyte values that are also in the first dataset, an evaluation data point is plotted on the control grid. The evaluation data point is determined by computing an evaluation median or average analyte value and an evaluation analyte variability value from the second dataset. Next, the magnitude of a vector that extends from the baseline data point to the evaluation data point is computed. Since any change in the value pair between the evaluation and baseline points may arise due to both true physiological change, such as the patient's ability to improve glycemic control, and a sensor fault, such as ESA, a mechanism is needed to isolate the latter for detection. For example, for sensing glucose, one method is to observe how patients can change their state of glycemic control over time, and correlate it with physiology-derived gradients that characterize this change. Examples of these gradients include gradients that quantify clinical risks such as hypoglycemia risk, retinopathy risk, or diabetic ketoacidosis risk. In some embodiments, contour lines representing varying degrees of hypoglycemic risk can be plotted on the control grid. Plotted contour lines can be used to graphically approximate the contour line that passes on to any point in the control grid. Alternatively, an analytical expression of these contour lines can be expressed in terms of a gradient function. In that case, the determination of a contour line passing through any point in the control grid is done by evaluating the gradient function. Next, a component of the magnitude of the vector between the points that is parallel to a hypoglycemia risk contour line is computed. In other words, a projection of the vector on the hypoglycemic risk contour line is computed. The component of the vector is compared to a predetermined threshold value. Values smaller than the threshold value indicate that the sensor is operating within an acceptable range. Values larger than the threshold value indicate that the sensor is operating in a fault mode or has reached the end of its operating life. The user is alerted to the fault condition and can be directed to replace the sensor. Alternatively, one or more reference measurements may be requested and a larger threshold value may be used to evaluate the status of the sensor. If the component of the vector is smaller than the larger threshold value, then the system indicates no failure detected. If the component of the vector is larger than the larger threshold value, then the system indicates the sensor should be replaced.

The invention may be applied to any analyte concentration level determination system that may exhibit or at least be suspected of exhibiting, or that may be susceptible to, in vivo sensor faults. Embodiments of the invention are described primarily with respect to continuous glucose monitoring devices and systems but the present disclosure may be applied to other analytes and analyte characteristics, as well as data from measurement systems that transmit sensor data from a sensor unit to another unit such as a processing or display unit in response a request from the other unit. For example, other analytes that may be monitored include, but are not limited to, acetyl choline, amylase, bilirubin, cholesterol, chorionic gonadotropin, creatine kinase (e.g., CK-MB), creatine, DNA, fructosamine, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times. The present disclosure also provides numerous additional embodiments.

Embodiments of the present disclosure may include a programmed computer system adapted to receive and store data from an analyte monitoring system. The computer system may include one or more processors for executing instructions or programs that implement the methods described herein. The computer system may include memory and persistent storage devices to store and manipulate the instructions and sensor data received from the analyte monitoring system. The computer system may also include communications facilities (e.g., wireless and/or wired) to enable transfer of the sensor data from the analyte monitoring system to the computer. The computer system may include a display and/or output devices for identifying dropouts in the sensor data to a user. The computer system may include input devices and various other components (e.g., power supply, operating system, clock, etc.) that are typically found in a conventional computer system. In some embodiments, the computer system may be integral to the analyte monitoring system. For example, the computer system may be embodied as a handheld or portable receiver unit within the analyte monitoring system.

The various methods described herein for performing one or more processes also described herein may be embodied as computer programs (e.g., computer executable instructions and data structures) developed using an object oriented programming language that allows the modeling of complex systems with modular objects to create abstractions that are representative of real world, physical objects and their interrelationships. However, any practicable programming language and/or techniques may be used. The software for performing the inventive processes, which may be stored in a memory or storage device of the computer system described herein, may be developed by a person of ordinary skill in the art based upon the present disclosure and may include one or more computer program products. The computer program products may be stored on a computer readable medium such as a server memory, a computer network, the Internet, and/or a computer storage device.

Turning now to FIG. 1, an example of a control grid 100 that depicts the states of patients with diabetes mellitus is shown. In the particular example shown, the control grid 100 provides a plot of a patients' glucose variability (on the x-axis) versus patients' median glucose concentration level (on the y-axis). Thus, each point is generated from a patient's sensor glucose data. In general, the patient's glycemic variability and median glucose are highly correlated. Contour or hypoglycemia risk lines 102, 104, 106 indicate a hypoglycemia risk gradient across the area of the control grid 100. In other words, moving in the direction of the solid arrow which is perpendicular to the hypoglycemia risk lines 102, 104, 106, each risk line 102, 104, 106 indicates a decreasing level of hypoglycemia risk for the patients whose plotted points lie closer to the upper left portion of the control grid. Thus, risk line 102 represents low hypoglycemia risk, risk line 104 represents intermediate hypoglycemia risk, and risk line 106 represents high hypoglycemia risk.

As a result of the correlation between glycemic variability and median glucose, patient data clusters in the band parallel to the hypoglycemia risk lines 102, 104, 106. The derivation and determination of the hypoglycemia risk lines 102, 104, 106 is described in detail in PCT Application No. PCT/US/ 2011/066610, filed on Dec. 21, 2011, entitled "Feedback for Cloud or HCP to Payer or Patient via Meter or Cellphone," and hereby incorporated herein by reference for all purposes.

Figure 2:
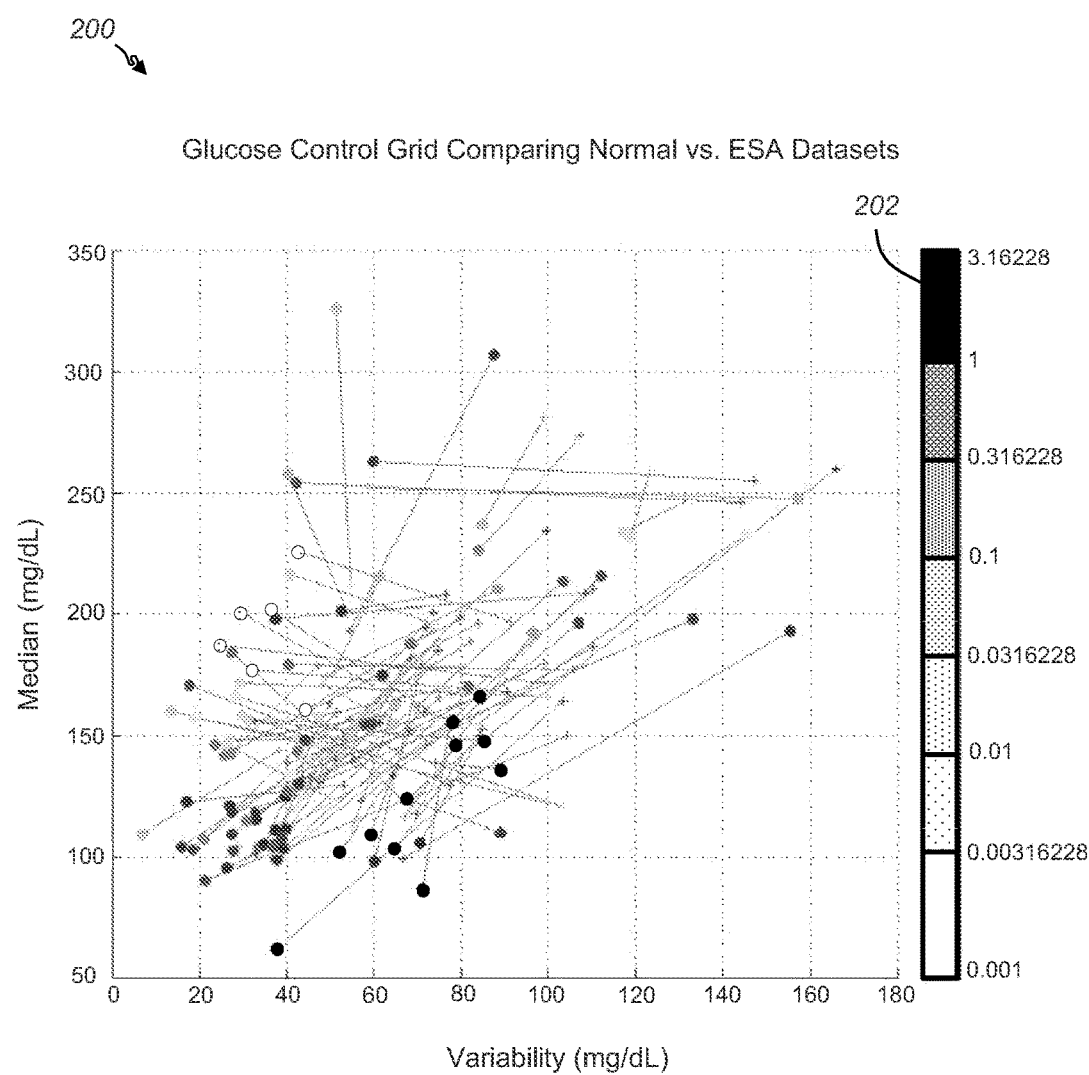
FIG. 2 depicts the example control grid of FIG. 1 with additional information in accordance with some embodiments of the present disclosure.
Figure 3:
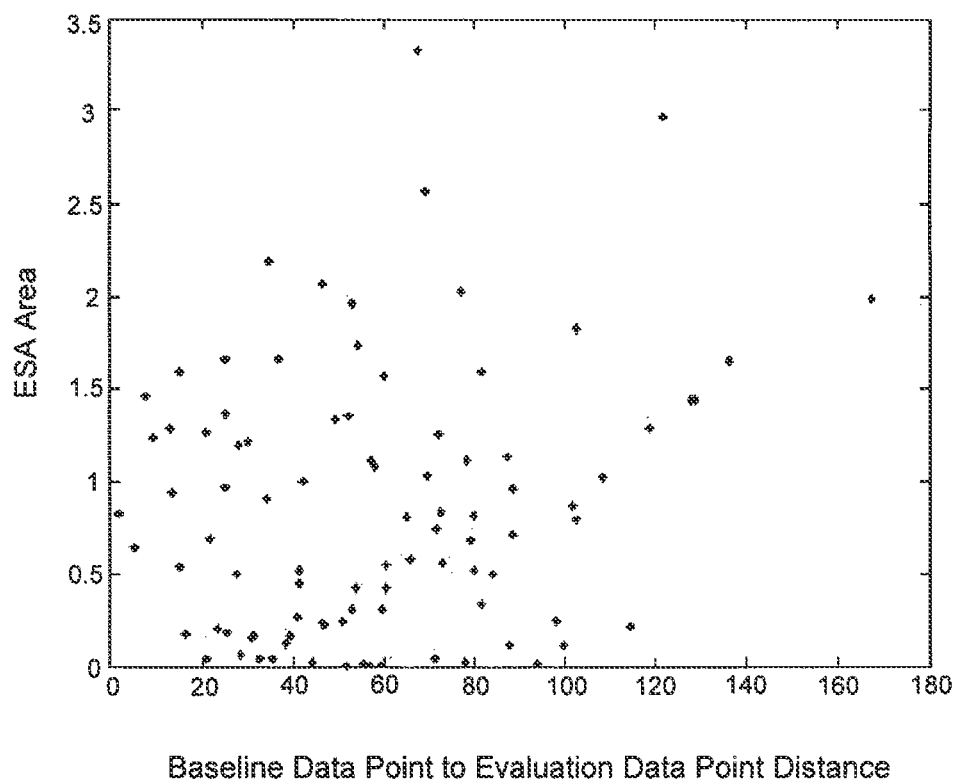
FIG. 3 depicts a graph of ESA severity versus baseline data point to evaluation data point distance in accordance with some embodiments of the present disclosure.
Figure 4A:
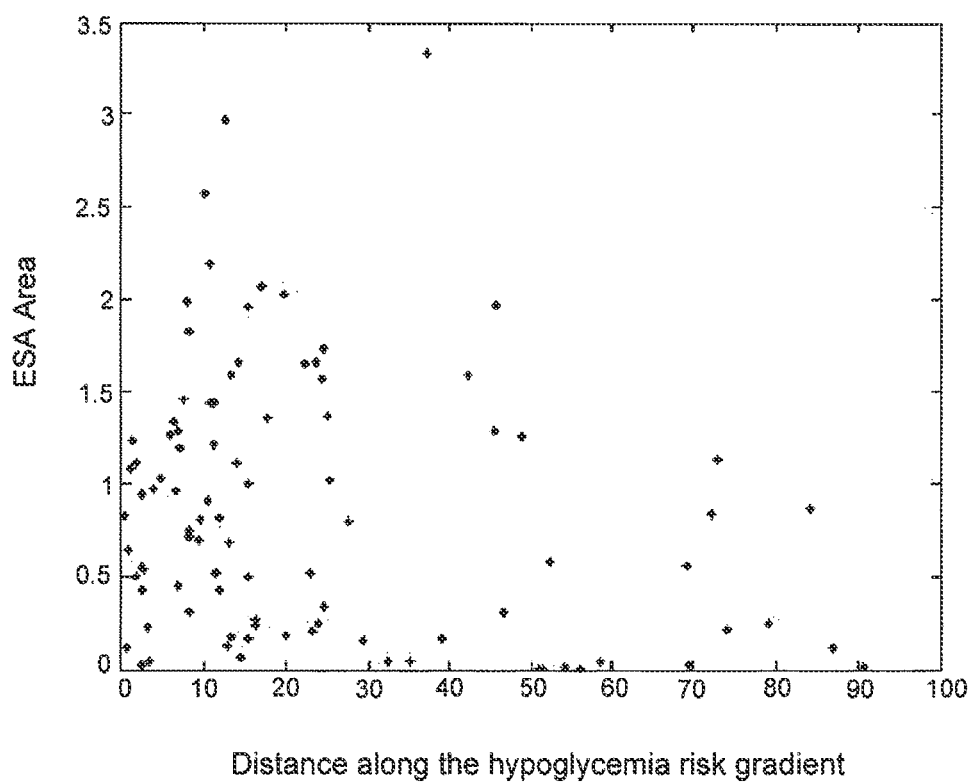
FIG. 4A depicts a graph of ESA severity versus distance along the hypoglycemia risk gradient in accordance with some embodiments of the present disclosure.

Turning to FIG. 2, a control grid 200 with the same patient data from FIG. 1 is shown but further including points (paired via a connecting line to the original points) that represent earlier sensor data from the same sensor that generated the data for the original points. The original points shift position on the control grid 200 towards the circle icons. The presence and severity of early signal attenuation (ESA) is represented by an ESA area metric and a scale 202. Darker denser patterns in the circle icons represent more severe ESA than circle icons with lighter less dense patterns. The distance between control grid values represented by the connecting lines in FIG. 2 for each sensor dataset can be compared against the ESA Area metric of the corresponding points. In general, sensors whose early wear period experiences more ESA, as represented by a larger ESA area, have larger late-to-early control grid distances. This correlation is illustrated in the graph 300 of FIG. 3. Examination of the data reveals that the component of this late-to-early distance perpendicular to the hypoglycemia risk lines (i.e. along the direction of the hypoglycemia risk gradient) has poor correlation to the ESA Area metric as shown in the graph 400A of FIG. 4A.

Figure 4B:
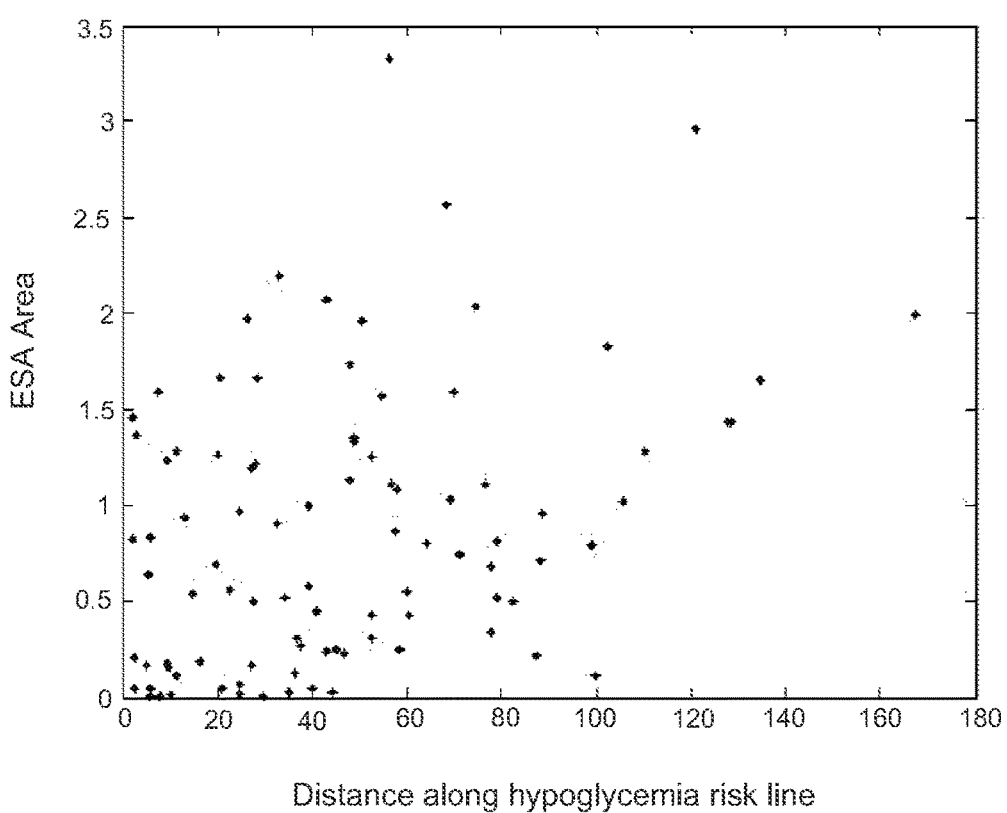
FIG. 4B depicts a graph of ESA severity versus distance along a hypoglycemia risk line in accordance with some embodiments of the present disclosure.

However, using only the component of the late-to-early distance along the hypoglycemia risk lines, the correlation to the ESA Area metric is improved. This can be seen by comparing the potential false positives when detecting ESA using a high value threshold based on the x-axis values of FIG. 4B as opposed to using a high value threshold based on the x-axis values of FIG. 4A. In other words, a vertical line can be drawn on the graph 400B of FIG. 4B that represents a threshold above which only points corresponding to severe ESA faults exist whereas no such line can be drawn on the graph 400A of FIG. 4A.

The present disclosure uses the above-described observations to recognize when a sensor is providing data that indicates the sensor is operating in a fault mode such as ESA or end of sensor life. When the projection of a vector from a baseline data point plotted on a control grid (e.g., depicting median analyte value versus analyte variability) to an evaluation point plotted on the same grid, along a risk line (e.g., a contour line of a risk gradient such as for example a hypoglycemia risk gradient), is larger than a threshold amount, the system of the present disclosure is operative to determine that the sensor is operating in a fault mode.

Figure 5B:
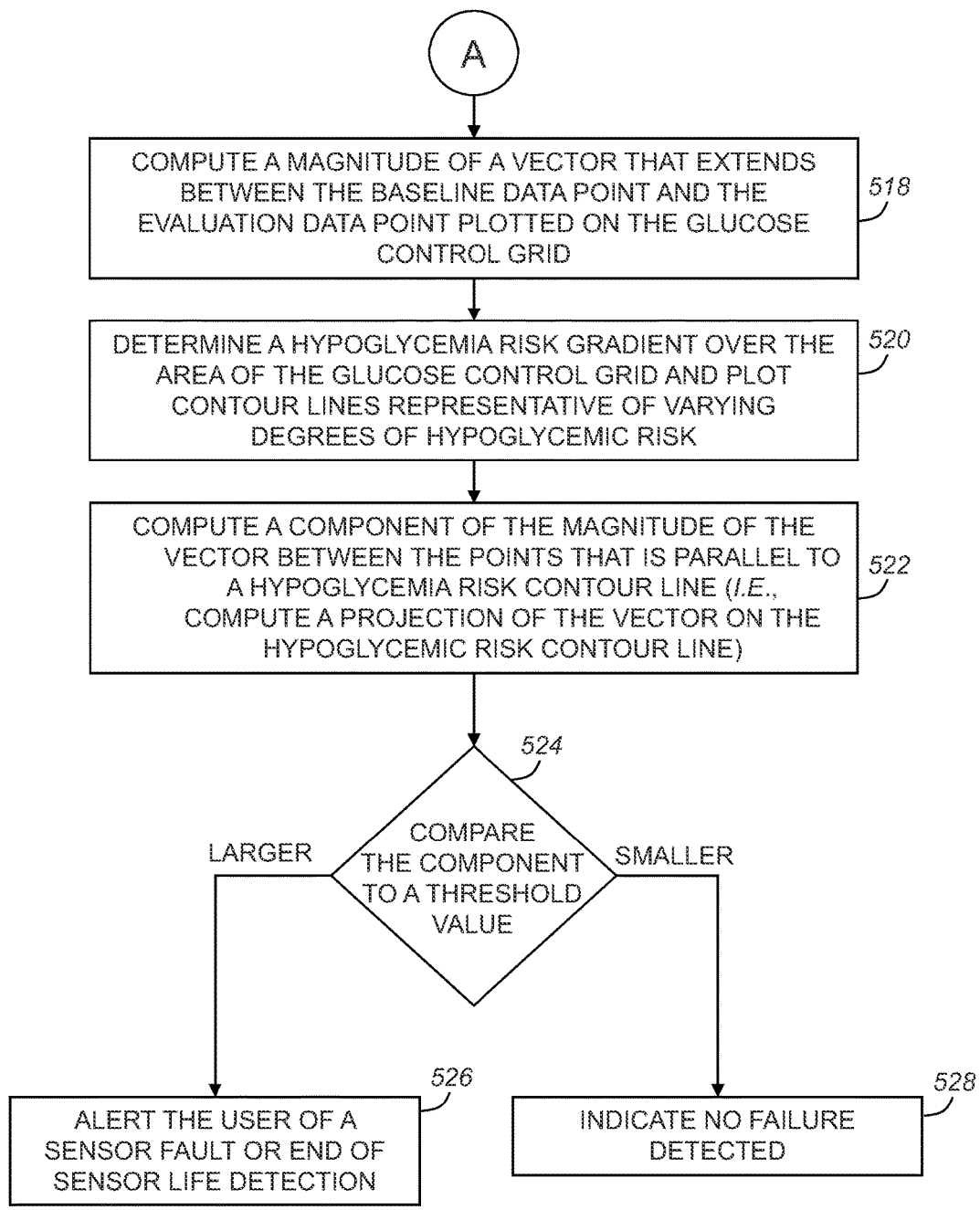

Turning now to FIGS. 5A and 5B, a flowchart depicting an example method 500 of detecting a sensor fault based on analyte sensor data pattern comparison is provided. As noted above, although the following example is described with respect to a glucose sensor, the invention is applicable to any analyte sensor. A first dataset of glucose values is received from sensor electronics coupled to a glucose sensor (502). Based on this first dataset, a baseline median glucose value is computed (504). Alternatively, a mean, a mode, or any other representative "static" value of the first dataset may be used. As used herein, the term median is intended to encompass all such possible values. Also based on this first dataset, a baseline glucose variability value is computed (506). A glucose variability value can be computed in a number of ways. For example, glucose variability may be computed by taking the difference between the median value and the 10th percentile value. Other methods and percentiles, such as standard deviation, inter quartile range, or other second moment calculation, can be used. Using the baseline median glucose value and the baseline glucose variability value as paired coordinate values on a glucose control grid, a baseline data point is plotted on the control grid (508). Alternatively, these values may simply be stored for later use in, for example, a memory.

A second dataset of glucose values is received from the sensor electronics coupled to a glucose sensor (510). To insure the accuracy of the present method, the second dataset should not include a significant number of sensor data that is also part of the first dataset. In other words, the datasets should not overlap in time. For example, the second dataset should have less than five percent of its glucose values in common with the first dataset. Based on this second dataset, an evaluation median glucose value is computed (512). Also based on the second dataset, an evaluation glucose variability value is computed (514). Using the evaluation median glucose value and the evaluation glucose variability value as coordinate values on the glucose control grid, an evaluation data point is plotted on the control grid (516). Alternatively, these values may simply be stored for later use in, for example, the memory.

Next, the magnitude of a vector extending from the baseline data point to the evaluation data point can be computed (518). A hypoglycemia risk gradient over the area of the glucose control grid is determined and risk contour lines representative of varying degrees of hypoglycemic risk are plotted (520). Alternatively, a hypoglycemia risk line that passes through the baseline data point may simply be stored in the memory of the system. A component of the magnitude of the vector extending between the data points that is parallel to one of the hypoglycemia risk contour lines is computed (522). In other words, a projection of the vector on the hypoglycemia risk contour line is computed. For example, the projection may be computed by taking the dot product between the vector extending from the baseline data point to the evaluation data point and a unit vector that describes the slope of the hypoglycemia risk contour lines. If the hypoglycemia risk contour lines are not parallel to each other, then the dot product between the vector and the unit vector that describes the local slope of the hypoglycemia risk line evaluated at the control grid coordinate of the baseline data point can be used.

Once the component of the magnitude that is parallel to a hypoglycemia risk contour line has been computed, it is compared to a threshold value (524). The threshold value may be determined a priori by analyzing a dataset from many patients spanning different levels of glycemic control, different percentages of overlap, and a good representation of nominal sensors and sensors with a fault. Different threshold values are evaluated for their false negatives and false positives. A threshold with appropriately low levels of false positive and false negative rates is chosen. If the component is larger than the threshold value, the system alerts the user that a fault has occurred or that the end of the sensor's life has been detected (526). If the component is smaller than the threshold value, the system indicates that the sensor is functioning properly (528).

Figure 6:
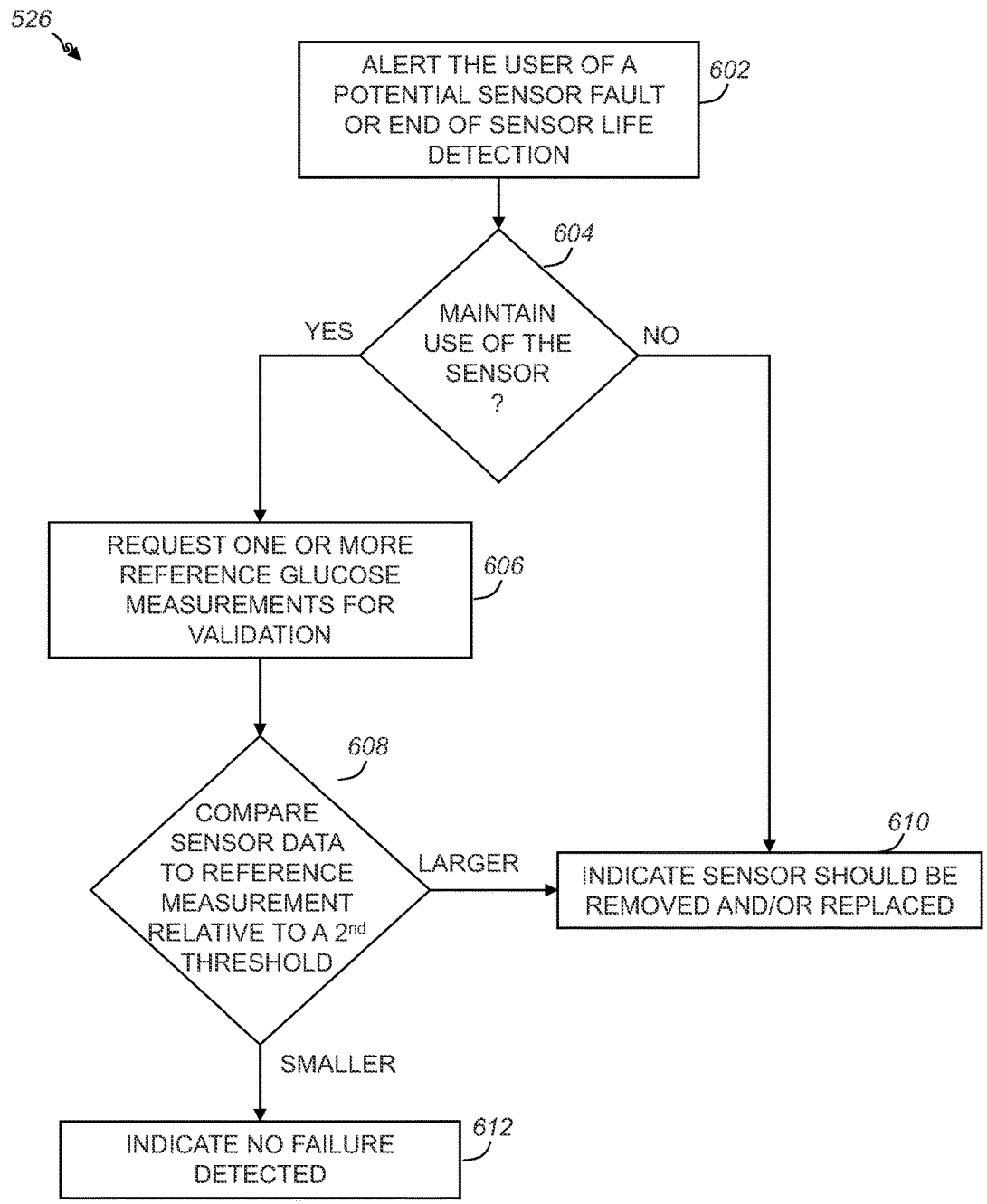
FIG. 6 depicts a flowchart illustrating example details of Box 526 of FIG. 5B in accordance with some embodiments of the present disclosure.

Turning now to FIG. 6, a flowchart depicting the details of alerting the user of a fault (526) is provided. In some embodiments, the system may initially alert the user that there is only a potential fault (602) and ask the user whether he would like to maintain use of the sensor if possible (604). If so, the system can request one or more in-vivo reference glucose measurements for validation (606). The system may then compare the sensor output to reference glucose measurement(s) relative to a second threshold. This second threshold is not related to the first threshold, in that the second threshold relates sensor output to reference glucose measurements. One example is to examine the difference between the latest sensor output value to the latest reference glucose measurement, and flag for a fault if the difference exceeds, for example, 15 mg/dL. Another example is to examine the ratio between the latest sensor output value to the latest reference glucose measurement, and flag for a fault if the ratio is lower than 0.85 or higher than 1.2. In these two examples, the values 15 mg/dL, 0.85, and 1.2 make up the set of second threshold values.

If the user does not wish to maintain use of the sensor or if the component is larger than the larger threshold value, then the system provides the user with an indication that the sensor should be removed and/or replaced (610). If the component is smaller than the larger threshold value, then the system indicates that no failure has been detected (612).

Figure 7A:
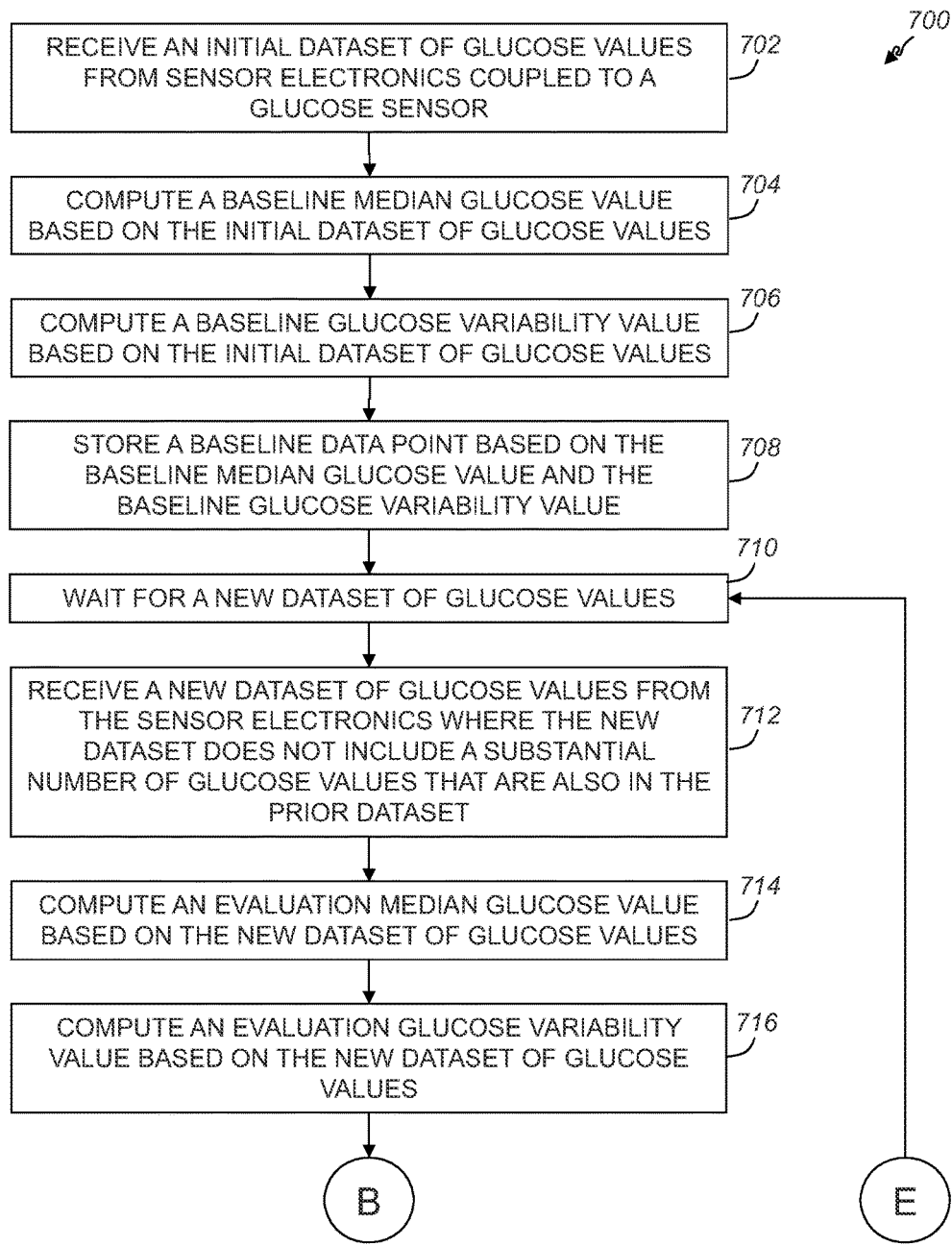
FIGS. 7A to 7C depict a flowchart illustrating an additional example method in accordance with some embodiments of the present disclosure.
Figure 7B:
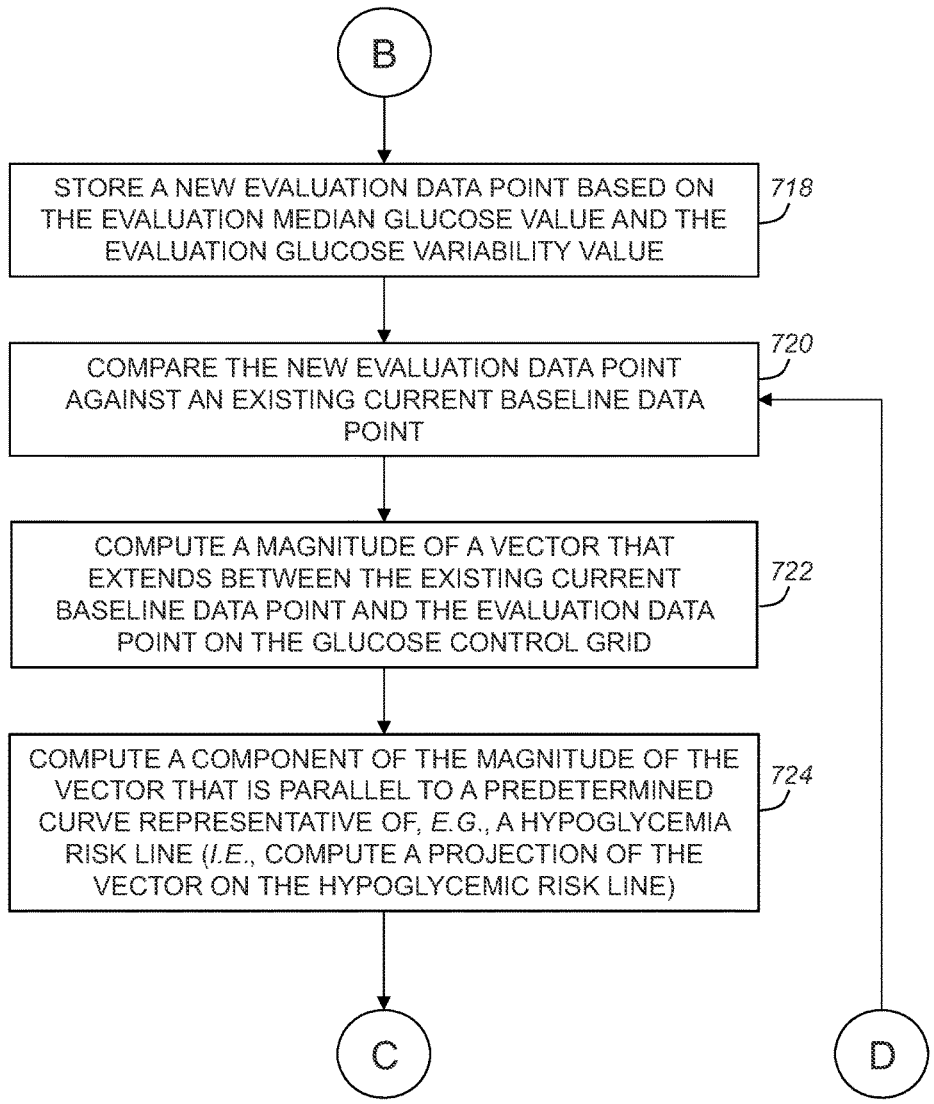
Figures 7A, 7B, 7C:
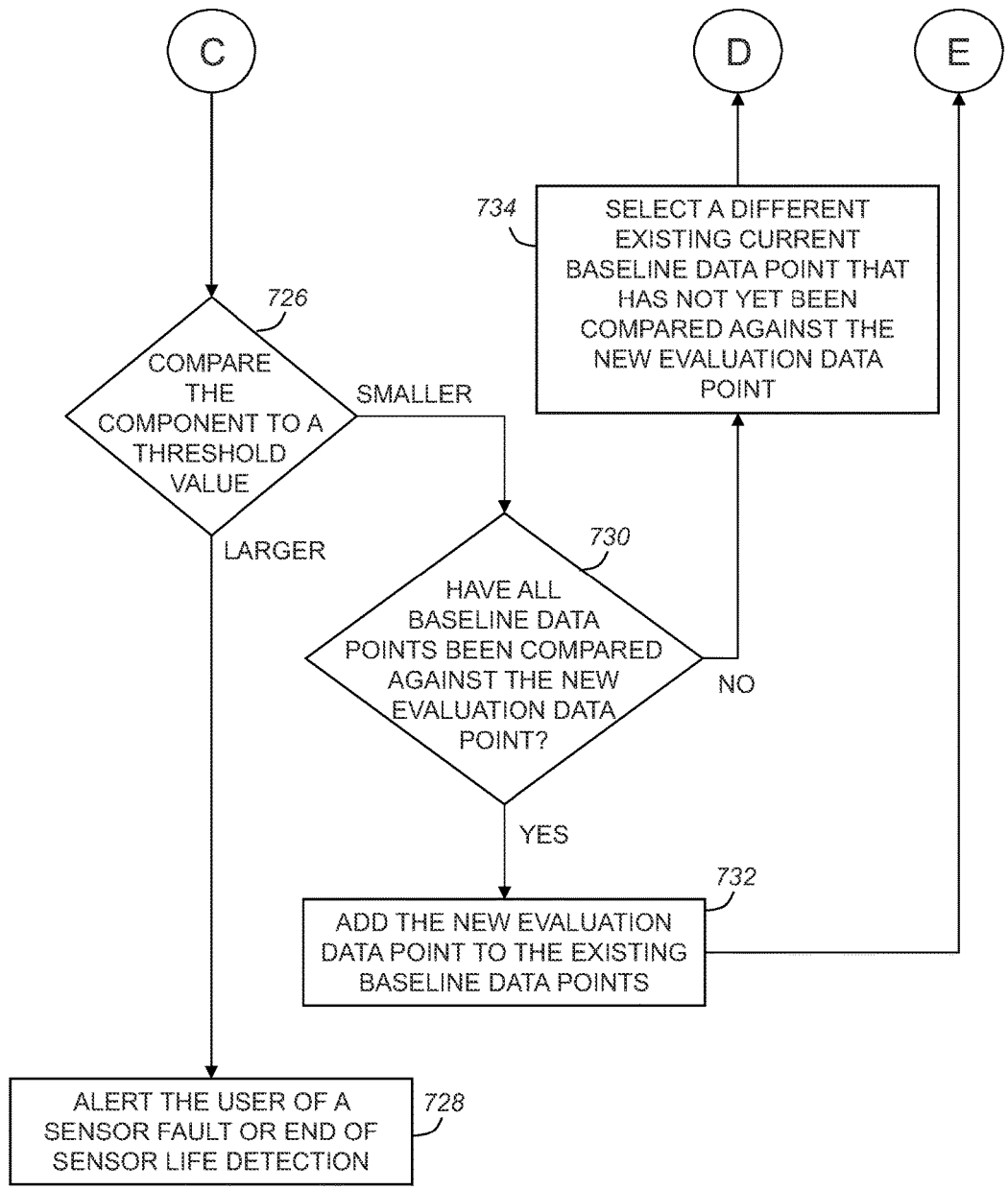

Turning now to FIGS. 7A to 7C, an iterative example embodiment of the method 700 of the present disclosure is provided. An initial dataset of glucose values is received from sensor electronics operatively coupled to a transcutaneously positioned glucose sensor (702). Based on this initial dataset, a baseline median glucose value is computed (704). Also based on the initial dataset of glucose values, a baseline glucose variability value is computed (706). A glucose variability value can be computed in a number of ways. For example, glucose variability may be computed by taking the difference between the median value and the 10th percentile value. Other methods and percentiles can be used. Using the baseline median glucose value and the baseline glucose variability value as coordinate values on a glucose control grid, a baseline data point is stored for later use in, for example, a memory (708). The system then waits for a new dataset of glucose values (710).

A new dataset of glucose values is received from the sensor electronics (712). To insure the accuracy of the present method, the new dataset should not include a significant number of sensor data that is also part of the prior dataset. In other words, the datasets should not overlap in time. For example, the new dataset should have less than five percent of its glucose values in common with the prior dataset. Based on this new dataset, an evaluation median glucose value is computed (714). Also based on the new dataset, an evaluation glucose variability value is computed (716). Using the evaluation median glucose value and the evaluation glucose variability value as coordinate values on the glucose control grid, a new evaluation data point is stored for later use in, for example, the memory (718).

Next, the new evaluation data point is compared against an existing current baseline data point (720). The magnitude of a vector extending from the existing current baseline data point to the new evaluation data point can be computed (722). A component of the magnitude of the vector extending between the data points that is parallel to a predetermined curve representative of, for example, a hypoglycemia risk line is computed (724). In other words, a projection of the vector on a hypoglycemic risk line is computed. For example, the projection may be computed by taking the dot product between the vector extending from the baseline data point to the evaluation data point and a unit vector that describes the slope of the hypoglycemia risk contour lines. If the hypoglycemia risk contour lines are not parallel to each other, then the dot product between the vector and the unit vector that describes the local slope of the hypoglycemia risk line evaluated at the control grid coordinate of the baseline data point can be used.

Once the component of the magnitude that is parallel to a hypoglycemia risk line has been computed, it is compared to a threshold value (726). The threshold value may be determined a priori by analyzing a dataset from many patients spanning different levels of glycemic control, different percentages of overlap, and a good representation of nominal sensors and sensors with a fault. Different threshold values are evaluated for their false negatives and false positives. A threshold with appropriately low levels of false positive and false negative rates is chosen. If the component is larger than the threshold value, the system alerts the user that a fault has occurred or that the end of the sensor's life has been detected (728). If the component is smaller than the threshold value, the system checks for additional baseline data points to compare with the new evaluation data point (730). If all baseline data points have been compared against the new evaluation data point, then the new evaluation data point is added to the existing baseline data points for future comparisons (732) and the system returns to waiting for another new dataset of glucose values (710). If all baseline data points have not been compared against the new evaluation data point, then a different existing baseline data point that has not yet been compared against the new evaluation data point is selected as the current baseline data point (734) and the system returns to comparing the new evaluation data point against the current baseline data point (720). Thus, the system will compare each new evaluation point against all of the baseline data points and if no fault is detected, the new evaluation data point becomes a baseline data point. Thereby, the collection of baseline data points grows with each new evaluation data point that does not indicate a fault.

In an alternate embodiment, the system and methods of the present disclosure can be used to retrospectively detect a fault mode such as ESA. In such embodiments, datasets representing sensor data measured during an "early sensor wear period" (e.g., the first ten to twenty-four hours from the time of sensor insertion) are used to compute evaluation data points that are compared against datasets representing sensor data measured after the early sensor wear period. The projection of the vector extending from the baseline data point to the evaluation data point along a hypoglycemia risk line is compared to a predefined threshold value as with previously described embodiments. However, the predefined threshold value may be different for detecting ESA than for detecting other faults. For example, the threshold value may be determined a priori by analyzing a dataset from many patients spanning different levels of glycemic control, different percentages of overlap, and a good representation of nominal sensors and sensors with ESA. Different threshold values are evaluated for their false negatives and false positives. A threshold with appropriately low levels of false positive and false negative rates is chosen. If the projection is larger than the predefined threshold, the data collected during the early sensor wear period is marked as invalid in the memory of the system. Where the user interface of the system allows for the viewing of any early sensor wear period data, the appropriate segments are indicated as invalid and an alert is issued to the user.

In the manner described above, in accordance with embodiments of the present disclosure, there is provided a computer-implemented method, comprising storing a baseline data point in a memory wherein the baseline data point is representative of a first point on a glucose control grid, storing an evaluation data point in the memory wherein the evaluation data point is representative of a second point on the glucose control grid, computing a magnitude of a vector that would extend between the baseline data point and the evaluation data point if plotted on the glucose control grid, defining a gradient function over an area of the glucose control grid and determining gradient contour lines around the baseline data point and the evaluation data point, computing a component of the magnitude of the vector between the baseline data point and the evaluation data point that is parallel to a contour line of the defined gradient function, comparing the component of the magnitude of the vector to a predefined threshold value, and displaying, on a system display, an indication that a sensor fault has been detected if the component of the magnitude of the vector is greater than a first predefined threshold value.

In certain embodiments, the baseline data point is determined based on using a baseline median glucose value and a baseline glucose variability value as coordinates for the baseline data point, and the baseline median glucose value and the baseline glucose variability value are computed by a processor based on a first dataset of glucose values received from a first data communication from sensor electronics operatively coupled to a transcutaneously positioned glucose sensor.

In certain embodiments, the evaluation data point is determined based on using an evaluation median glucose value and an evaluation glucose variability value as coordinates for the evaluation data point, and the evaluation median glucose value and the evaluation glucose variability value are computed using the processor based on a second dataset of glucose values received from a second data communication from the sensor electronics operatively coupled to the transcutaneously positioned glucose sensor, where the second dataset of glucose values includes glucose values that are not in the first dataset of glucose values.

In certain embodiments, the computer-implemented method further includes displaying, on the system display, the indication that the sensor fault has not been detected if the component of the magnitude of the vector is less than the first predefined threshold value.

In certain embodiments, displaying the indication that the sensor fault has been detected further includes prompting a user to indicate whether to maintain use of a glucose sensor.

In certain embodiments, displaying the indication that the sensor fault has been detected further includes requesting a reference glucose measurement for validation.

In certain embodiments, displaying the indication that the sensor fault has been detected further includes comparing sensor output to the reference glucose measurement relative to a second predefined threshold value.

In certain embodiments, displaying the indication that the sensor fault has been detected further includes displaying, on the system display, an indication to remove the glucose sensor if the component of the magnitude of the vector is greater than a second predefined threshold value.

A system for determining analyte concentration in blood based on analyte concentration measured in interstitial fluid in certain embodiments includes a processor, and a memory coupled to the processor, the memory storing processor executable instructions to: store a baseline data point in the memory wherein the baseline data point is representative of a first point on an analyte control grid, store an evaluation data point in the memory wherein the evaluation data point is representative of a second point on the analyte control grid, compute a magnitude of a vector that would extend between the baseline data point and the evaluation data point if plotted on the analyte control grid, define a gradient function over an area of the analyte control grid and determine gradient contour lines around the baseline data point and the evaluation data point, compute a component of the magnitude of the vector between the baseline data point and the evaluation data point that is parallel to a contour line of the defined gradient function, compare the component of the magnitude of the vector to a predefined threshold value, display, on a system display, an indication that a sensor fault has been detected if the component of the magnitude of the vector is greater than a first predefined threshold value.

In certain embodiments, the memory is further configured to store processor executable instructions to: receive a first dataset of analyte values from sensor electronics operatively coupled to a transcutaneously positioned analyte sensor, compute a baseline median analyte value based on the first dataset of analyte values, compute a baseline analyte variability value based on the first dataset of analyte values, determine the baseline data point based on using the baseline median analyte value and the baseline analyte variability value as coordinates for the baseline data point on the analyte control grid.

In certain embodiments, the memory is further configured to store processor executable instructions to: receive a second dataset of analyte values from the sensor electronics where the second dataset of analyte values includes analyte values that are not in the first dataset of analyte values, compute an evaluation median analyte value based on the second dataset of analyte values, compute an evaluation analyte variability value based on the second dataset of analyte values, determine the evaluation data point based on using the evaluation median analyte value and the evaluation analyte variability value as coordinates for the evaluation data point on the analyte control grid.

In certain embodiments, the memory is further configured to store processor executable instructions to display, on the system display, the indication that the sensor fault has not been detected if the component of the magnitude of the vector is less than the first predefined threshold value.

In certain embodiments, the memory is further configured to store processor executable instructions to display, on the system display, the indication that the sensor fault has been detected further includes an instruction to prompt a user to indicate whether to maintain use of a sensor.

In certain embodiments, the instruction to display, on the system display, the indication that the sensor fault has been detected further includes an instruction to request a reference glucose measurement for validation.

In certain embodiments, the instruction to display, on the system display, the indication that the sensor fault has been detected further includes an instruction to compare sensor output to the reference glucose measurement relative to a second predefined threshold value.

In certain embodiments, the instruction to display, on the system display, the indication that the sensor fault has been detected further includes an instruction to display, on the system display, an indication to remove the sensor if the component of the magnitude of the vector is greater than the second predefined threshold value.

A computer-implemented method in certain embodiments includes storing an evaluation data point representative of a first point on a glucose control grid, storing a baseline data point representative of a second point on the glucose control grid, computing a magnitude of a vector that extends between the baseline data point and the evaluation data point, defining a gradient function over an area of the glucose control grid including determining at least one gradient contour line around the baseline data point and the evaluation data point, computing a component of the magnitude of the vector between the baseline data point and the evaluation data point that is parallel to a contour line of the defined gradient function, comparing the component of the magnitude of the vector to a predefined threshold value, displaying, on a system display, an indication that an early signal attenuation (ESA) fault has been detected if the component of the magnitude of the vector is greater than a first predefined threshold value.

In certain embodiments, the method further includes receiving during an early wear period, a first dataset of glucose values from sensor electronics operatively coupled to a transcutaneously positioned glucose sensor, computing an evaluation median glucose value based on the first dataset of glucose values, computing an evaluation glucose variability value based on the first dataset of glucose values, determining the evaluation data point based on using the evaluation median glucose value and the evaluation glucose variability value as coordinates for the evaluation data point on the glucose control grid.

In certain embodiments, the method further comprises receiving after the early wear period a second dataset of glucose values from the sensor electronics where the second dataset of glucose values does not include glucose values that are also in the first dataset of glucose values, computing a baseline median glucose value based on the second dataset of glucose values, computing a baseline glucose variability value based on the second dataset of glucose values, and determining the baseline data point based on using the baseline median glucose value and the baseline glucose variability value as coordinates for the baseline data point on the glucose control grid.

In certain embodiments, the method further comprises displaying the indication that the early signal attenuation (ESA) fault has not been detected if the component of the magnitude of the vector is less than the first predefined threshold value.

In certain embodiments, the method further comprises displaying the indication that the early signal attenuation (ESA) fault has been detected further includes prompting a user whether to maintain use of a glucose sensor.

In certain embodiments, the method further comprises displaying the indication that the early signal attenuation (ESA) fault has been detected further includes requesting a reference glucose measurement for validation.

In certain embodiments, displaying the indication that the early signal attenuation (ESA) fault has been detected further includes comparing sensor output to the reference glucose measurement relative to a second predefined threshold value.

In certain embodiments, displaying the indication that the early signal attenuation (ESA) fault has been detected further includes displaying, on the system display, an indication that a first dataset of glucose values are invalid.

In certain embodiments, the method further comprises storing the evaluation data point as the baseline data point if no fault is detected for the evaluation data point.

In certain embodiments, the method further comprises comparing the evaluation data point against multiple baseline data points.

Various other modifications and alterations in the structure and method of operation of the embodiments of the present disclosure will be apparent to those skilled in the art without departing from the scope and spirit of the present disclosure. Although the present disclosure has been described in connection with certain embodiments, it should be understood that the present disclosure as claimed should not be unduly limited to such embodiments. It is intended that the following claims define the scope of the present disclosure and that structures and methods within the scope of these claims and their equivalents be covered thereby.

What is claimed is:
1. A computer-implemented method, comprising:
    storing a baseline data point in a memory wherein the baseline data point is representative of a first point on a glucose control grid;
    storing an evaluation data point in the memory wherein the evaluation data point is representative of a second point on the glucose control grid;
    computing a magnitude of a vector that would extend between the baseline data point and the evaluation data point if plotted on the glucose control grid;
    defining a gradient function over an area of the glucose control grid and determining gradient contour lines around the baseline data point and the evaluation data point;

computing a component of the magnitude of the vector between the baseline data point and the evaluation data point that is parallel to a contour line of the defined gradient function;

comparing the component of the magnitude of the vector to a first predefined threshold value;

displaying, on a system display, an indication that a sensor fault has been detected if the component of the magnitude of the vector is greater than the first predefined threshold value; and displaying, on the system display, an indication that the sensor fault has not been detected if the component of the magnitude of the vector is less than the first predefined threshold value.

2. The computer-implemented method of claim 1, wherein the baseline data point is determined based on using a baseline median glucose value and a baseline glucose variability value as coordinates for the baseline data point; and further wherein the baseline median glucose value and the baseline glucose variability value are computed by a processor based on a first dataset of glucose values received from a first data communication from sensor electronics operatively coupled to a transcutaneously positioned glucose sensor.

3. The computer-implemented method of claim 2, wherein the evaluation data point is determined based on using an evaluation median glucose value and an evaluation glucose variability value as coordinates for the evaluation data point; and further wherein the evaluation median glucose value and the evaluation glucose variability value are computed using the processor based on a second dataset of glucose values received from a second data communication from the sensor electronics operatively coupled to the transcutaneously positioned glucose sensor, where the second dataset of glucose values includes glucose values that are not in the first dataset of glucose values.

4. The computer-implemented method of claim 1, wherein displaying, on the system display, the indication that the sensor fault has been detected further includes prompting a user to indicate whether to maintain use of a glucose sensor.

5. The computer-implemented method of claim 4, wherein displaying, on the system display, the indication that the sensor fault has been detected further includes requesting a reference glucose measurement for validation.

6. The computer-implemented method of claim 5, wherein displaying, on the system display, the indication that the sensor fault has been detected further includes comparing sensor output to the reference glucose measurement relative to a second predefined threshold value.

7. The computer-implemented method of claim 5, wherein displaying, on the system display, the indication that the sensor fault has been detected further includes displaying, on the system display, an indication to remove the glucose sensor if the component of the magnitude of the vector is greater than a second predefined threshold value.

8. A system for determining analyte concentration in blood based on analyte concentration measured in interstitial fluid, the system comprising:

a processor; and a memory coupled to the processor, the memory storing processor executable instructions to:

store a baseline data point in the memory wherein the baseline data point is representative of a first point on an analyte control grid;

store an evaluation data point in the memory wherein the evaluation data point is representative of a second point on the analyte control grid;

compute a magnitude of a vector that would extend between the baseline data point and the evaluation data point if plotted on the analyte control grid;

define a gradient function over an area of the analyte control grid and determine gradient contour lines around the baseline data point and the evaluation data point;

compute a component of the magnitude of the vector between the baseline data point and the evaluation data point that is parallel to a contour line of the defined gradient function;

compare the component of the magnitude of the vector to a first predefined threshold value;

display, on a system display, an indication that a sensor fault has been detected if the component of the magnitude of the vector is greater than the first predefined threshold value; and display, on the system display, an indication that the sensor fault has not been detected if the component of the magnitude of the vector is less than the first predefined threshold value.

9. The system of claim 8, wherein the memory is further configured to store processor executable instructions to:

receive a first dataset of analyte values from sensor electronics operatively coupled to a transcutaneously positioned analyte sensor;

compute a baseline median analyte value based on the first dataset of analyte values;

compute a baseline analyte variability value based on the first dataset of analyte values; and determine the baseline data point based on using the baseline median analyte value and the baseline analyte variability value as coordinates for the baseline data point on the analyte control grid.

10. The system of claim 9, wherein the memory is further configured to store processor executable instructions to:

receive a second dataset of analyte values from the sensor electronics where the second dataset of analyte values includes analyte values that are not in the first dataset of analyte values;

compute an evaluation median analyte value based on the second dataset of analyte values;

compute an evaluation analyte variability value based on the second dataset of analyte values; and determine the evaluation data point based on using the evaluation median analyte value and the evaluation analyte variability value as coordinates for the evaluation data point on the analyte control grid.

11. The system of claim 8, wherein the memory is further configured to store processor executable instructions to display, on the system display, the indication that the sensor fault has been detected and further includes an instruction to prompt a user to indicate whether to maintain use of a sensor.

12. The system of claim 11, wherein the instruction to display, on the system display, the indication that the sensor fault has been detected further includes an instruction to request a reference glucose measurement for validation.

13. The system of claim 12, wherein the instruction to display, on the system display, the indication that the sensor fault has been detected further includes an instruction to compare sensor output to the reference glucose measurement relative to a second predefined threshold value.

14. The system of claim 13, wherein the instruction to display, on the system display, the indication that the sensor fault has been detected further includes an instruction to display, on the system display, an indication to remove the sensor if the component of the magnitude of the vector is greater than the second predefined threshold value.

15. A computer-implemented method, comprising:
storing an evaluation data point representative of a first point on a glucose control grid;
storing a baseline data point representative of a second point on the glucose control grid;
computing a magnitude of a vector that extends between the baseline data point and the evaluation data point;
defining a gradient function over an area of the glucose control grid including determining at least one gradient contour line around the baseline data point and the evaluation data point;
computing a component of the magnitude of the vector between the baseline data point and the evaluation data point that is parallel to a contour line of the defined gradient function;
comparing the component of the magnitude of the vector to a first predefined threshold value;
displaying, on a system display, an indication that an early signal attenuation (ESA) fault has been detected if the component of the magnitude of the vector is greater than the first predefined threshold value; and
displaying, on the system display, an indication that the early signal attenuation (ESA) fault has not been detected if the component of the magnitude of the vector is less than the first predefined threshold value.

16. The computer-implemented method of claim 15, further comprising:
receiving during an early wear period, a first dataset of glucose values from sensor electronics operatively coupled to a transcutaneously positioned glucose sensor;
computing an evaluation median glucose value based on the first dataset of glucose values;
computing an evaluation glucose variability value based on the first dataset of glucose values; and
determining the evaluation data point based on using the evaluation median glucose value and the evaluation glucose variability value as coordinates for the evaluation data point on the glucose control grid.

17. The computer-implemented method of claim 16, further comprising:
receiving after the early wear period a second dataset of glucose values from the sensor electronics where the second dataset of glucose values does not include glucose values that are also in the first dataset of glucose values;
computing a baseline median glucose value based on the second dataset of glucose values;
computing a baseline glucose variability value based on the second dataset of glucose values; and
determining the baseline data point based on using the baseline median glucose value and the baseline glucose variability value as coordinates for the baseline data point on the glucose control grid.

18. The computer-implemented method of claim 15, wherein displaying, on the system display, the indication that the early signal attenuation (ESA) fault has been detected further includes prompting a user whether to maintain use of a glucose sensor.

19. The computer-implemented method of claim 18, wherein displaying, on the system display, the indication that the early signal attenuation (ESA) fault has been detected further includes requesting a reference glucose measurement for validation.

20. The computer-implemented method of claim 19, wherein displaying, on the system display, the indication that the early signal attenuation (ESA) fault has been detected further includes comparing sensor output to the reference glucose measurement relative to a second predefined threshold value.

21. The computer-implemented method of claim 20, wherein displaying, on the system display, the indication that the early signal attenuation (ESA) fault has been detected further includes displaying, on the system display, an indication that a first dataset of glucose values are invalid.

22. The computer-implemented method of claim 15, further comprising storing the evaluation data point as the baseline data point if no fault is detected for the evaluation data point.

23. The computer-implemented method of claim 22, further comprising comparing the evaluation data point against multiple baseline data points.

* * * * *